(12) United States Patent
Ziegler et al.

(10) Patent No.: US 6,372,787 B1
(45) Date of Patent: Apr. 16, 2002

(54) PHENYL-METHOXYIMINO-GLYOXYLIC ACID DERIVATIVES AS PESTICIDES

(75) Inventors: Hugo Ziegler, Witterswil; René Zurflüh, Bülach, both of (CH)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/671,421

(22) Filed: Sep. 27, 2000

Related U.S. Application Data

(63) Continuation of application No. PCT/EP99/02037, filed on Mar. 25, 1999.

(30) Foreign Application Priority Data

Mar. 27, 1998 (CH) .............................................. 0735/98

(51) Int. Cl.[7] ....................... C07C 229/40; A01N 37/10; A01N 37/50; A01N 37/52
(52) U.S. Cl. ..................................................... 514/538
(58) Field of Search ............................. 560/35; 514/538

(56) References Cited

FOREIGN PATENT DOCUMENTS

| JP | 10-025271 | * | 1/1998 | ......... C07C/251/48 |
|---|---|---|---|---|
| WO | WO-00/53585 | * | 9/2000 | ......... C07D/249/12 |

* cited by examiner

*Primary Examiner*—Gary Geist
*Assistant Examiner*—M. P. Moon

(74) *Attorney, Agent, or Firm*—Joseph C. Gil

(57) ABSTRACT

Compounds of formula I

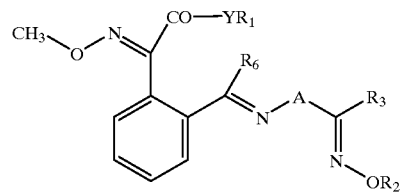

wherein

A is a group $OCHR_4$ or $N=CR_4$;

Y is O or NH, $R_1$ is $C_1$–$C_6$-alkyl;

$R_2$ is $C_1$–$C_6$-alkyl or $C_1$–$C_6$-alkyl substituted by 1 to 5 fluorine atoms;

$R_3$ is $C_1$–$C_6$-alkyl, $C_1$–$C_6$-alkoxy, $C_3$–$C_6$-cycloalkyl, $C_3$–$C_6$-cycloalkoxy, $C_2$–$C_6$-alkenyl, $C_2$–$C_6$-alkenyloxy, $C_2$–$C_6$-alkinyl, $C_2$–$C_6$-alkinyloxy, $C_1$–$C_6$-alkoxycarbonyl, CN or halogen, aryl, hetaryl, heterocyclyl, aryloxy, hetaryloxy or heterocyclyloxy, whereby the above-mentioned groups, with the exception of CN and halogen, may be substituted by the same or different substituents;

$R_4$ is methyl, ethyl or cyclopropyl;

$R_6$ is hydrogen or methyl;

have microbicidal, insecticidal and acaricidal activity, and may be used to control plant-pathogenic fungi, acarids and insects in agriculture and in the field of hygiene.

17 Claims, No Drawings

PHENYL-METHOXYIMINO-GLYOXYLIC ACID DERIVATIVES AS PESTICIDES

This is a continuation of International Application No. PCT/EP99/02037, filed Mar. 25, 1999, the contents of which are incorporated herein by reference.

The present invention relates to new 2-phenyl-methoxyimino-glyoxylic acid derivatives having microbicidal, insecticidal and acaricidal activity, a process for the preparation thereof, new intermediates for the preparation thereof, agrochemical compositions containing these active ingredients, as well as their usage in the control and prevention of plant-pathogenic fungi, acarids and insects in agriculture and in the field of hygiene.

The new compounds correspond to formula I wherein

A is a group $OCHR_4$ or $N=CR_4$;

Y is O or NH, $R_1$ is $C_1$–$C_6$-alkyl;

$R_2$ is $C_1$–$C_6$-alkyl or $C_1$–$C_6$-alkyl substituted by 1 to 5 fluorine atoms;

$R_3$ is $C_1$–$C_6$-alkyl, $C_1$–$C_6$-alkoxy, $C_3$–$C_6$-cycloalkyl, $C_3$–$C_6$-cycloalkoxy, $C_2$–$C_6$-alkenyl, $C_2$–$C_6$-alkenyloxy, $C_2$–$C_6$-alkynyl, $C_2$–$C_6$-alkynyloxy, $C_1$–$C_6$-alkoxycarbonyl, CN or halogen, whereby the above-mentioned groups, with the exception of CN and halogen, may be substituted by one or more identical or different substitutents selected from the group comprising halogen, cyano, nitro, $C_1$–$C_6$-alkoxycarbonyl, $C_1$–$C_6$-alkoxy, $C_1$–$C_6$-alkylthio, aminocarbonyl, $C_1$–$C_6$-alkylaminocarbonyl, di-$C_1$–$C_6$-alkylaminocarbonyl, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, heteroaryl, heteroaryloxy, whereby the cyclic radicals in turn may be substituted by one or more identical or different substitutents selected from the group comprising halogen, cyano, nitro, $C_1$–$C_6$-alkyl, $C_1$–$C_6$halogenoalkyl, $C_1$–$C_6$-alkoxy, $C_1$–$C_6$-halogenoalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, optionally substituted benzyl, optionally substituted benzyloxy, optionally substituted aryl, optionally substituted aryloxy, optionally substituted heteroaryl and optionally substituted heteroaryloxy, whereby the optionally substituted aromatic groups are unsubstituted or mono- to tri-substituted by the same or different substituents selected from halogen, $C_1$–$C_6$-alkyl, $C_1$–$C_6$-halogenoalkyl, $C_1$–$C_6$-alkoxy, $C_1$–$C_6$-halogenoalkoxy, $C_2$–$C_6$-alkenyl, $C_2$–$C_6$-alkenyloxy, $C_2$–$C_6$-alkynyl, $C_3$–$C_6$-alkynyloxy, $C_1$–$C_6$-alkoxycarbonyl, CN or OCN; or $R_3$ is aryl, heteroaryl, heterocyclyl, aryloxy, heteroaryloxy or heterocyclyloxy, whereby the above-mentioned groups may be substituted by one or more identical or different substituents selected from the group comprising halogen, $C_1$–$C_6$-alkoxy, halogeno-$C_1$–$C_6$-alkoxy, $C_1$–$C_6$-alkylthio, halogeno-$C_1$–$C_6$-alkylthio, $C_1$–$C_6$-alkylsulfinyl, halogeno-$C_1$–$C_6$-alkylsulfinyl, $C_1$–$C_6$-alkylsulfonyl, halogeno-$C_1$–$C_6$-alkylsulfonyl, $C_1$–$C_6$-alkylcarbonyl, halogeno-$C_1$–$C_6$-alkylcarbonyl, $C_1$–$C_6$-alkoxycarbonyl, halogeno-$C_1$–$C_6$-alkoxycarbonyl, $C_1$–$C_6$-alkylamino-carbonyl, di-($C_1$–$C_6$-alkyl)-aminocarbonyl, whereby the alkyl groups may be identical or different, $C_1$–$C_6$-alkylaminothiocarbonyl, di-($C_1$–$C_6$-alkyl)-aminothiocarbonyl, whereby the alkyl groups may be identical or different, $C_1$–$C_6$-alkylamino, di-($C_1$–$C_6$-alkyl)-amino, $NO_2$, an unsubstituted $C_1$–$C_4$-alkylenedioxy group or one which is substituted once to four times by $C_1$–$C_4$-alkyl and/or by halogen, or CN, $SF_3$ and $QR_5$;

Q is a direct bond, O, O($C_1$–$C_6$-alkylene), ($C_1$–$C_6$-alkylene)O, S(=O)p, S(=O)p($C_1$–$C_6$-alkylene), ($C_1$–$C_6$-alkylene)S(=O)p, $C_1$–$C_8$-alkylene, $C_2$–$C_6$-alkenylene or $C_2$–$C_6$-alkynylene;

$R_5$ is a $C_2$–$C_6$-alkenyl or $C_2$–$C_6$-alkynyl group either unsubstituted or substituted by 1 to 3 halogen atoms, a ($C_1$–$C_4$-alkyl)$_3$Si group, whereby the alkyl groups may be identical or different, CN, an unsubstituted or mono- to penta-substituted $C_3$–$C_6$-cycloalkyl, aryl, hetaryl or heterocyclyl group, whereby the substituents are selected from the group comprising halogen, $C_1$–$C_6$-alkyl, halogeno-$C_1$–$C_6$-alkyl, $C_1$–$C_6$-alkoxy, halogeno-$C_1$–$C_6$-alkoxy, phenoxy and CN;

p is 0, 1 or 2;

$R_4$ is methyl, ethyl or cyclopropyl;

$R_6$ is hydrogen or methyl.

Formula I should include all the possible isomeric forms, as well as mixtures, e.g. racemic mixtures, and any [E/Z] mixtures.

Alkyl—as a group per se and as a structural element of other groups and compounds, such as halogenoalkyl, alkoxy and alkylthio—is either straight-chained, i.e. methyl, ethyl, propyl, butyl, pentyl or hexyl, or branched, e.g. isopropyl, isobutyl, sec.-butyl, tert.-butyl, isopentyl, neopentyl or isohexyl.

Alkenyl—as a group per se se and as a structural element of other groups and compounds, such as halogenoalkenyl—is either straight-chained, for example vinyl, 1-methylvinyl, allyl, 1-butenyl or 2-hexenyl, or branched, for example isopropenyl.

Alkynyl—as a group per se and as a structural element of other groups and compounds, such as halogenoalkynyl—is either straight-chained, for example propargyl, 2-butynyl or 5-hexynyl, or branched, for example 2-ethynylpropyl or 2-propargylisopropyl.

Alkylenedioxy is —O(alkylene)O—.

Alkylene—as a group per se and as a structural element of other groups and compounds, such as O(alkylene), (alkylene)O, S(=O)p(alkylene), (alkylene)S(=O)p or alkylenedioxy— is either straight-chained, for example —$CH_2CH_2$—, —$CH_2CH_2CH_2$— or —$CH_2CH_2CH_2CH_2$—, or branched, for example —CH($CH_3$)—, —CH($C_2H_5$)—, —C($CH_3$)$_2$—, —CH($CH_3$)$CH_2$— or —CH($CH_3$)CH($CH_3$)—.

Alkenylene is either straight-chained, for example vin-1,2-ylene, all-1,3-ylene, but-1-en-1,4-ylene or hex-2-en-1,6-ylene, or branched, for example 1-methylvin-1,2-ylene.

Alkynylene is either straight-chained, for example propargylene, 2-butynylene or 5-hexynylene, or branched, for example 2-ethynylpropylene or 2-propargylisopropylene.

Halogen is fluorine, chlorine, bromine or iodine, preferably fluorine, chlorine or bromine. Halogenoalkyl may contain indentical or different halogen atoms.

Aryl is phenyl or naphthyl, preferably phenyl.

Heteroaryl is a cyclic aromatic group with 5 to 9 ring members in one or two rings, 1 to 3 members of which are hetero atoms, selected from the group oxygen, sulphur and nitrogen. 1 to 2 benzene rings may be condensed onto the heterocycle, whereby the binding to the residual molecule takes place either via the hetero or the benzene moiety.

Examples are benzimidazolyl, benzisoxazolyl, benzisothiazolyl, benzocoumarinyl, benzofuryl, benzothiadiazolyl, benzothiazolyl, benzothienyl, benzoxazolyl, benzoxdiazolyl, quinazolinyl, quinolyl, quinoxalinyl, carbazolyl, dihydrobenzofuryl, furyl, imidazolyl, indazolyl, indolyl, isoquinolinyl, isothiazolyl, isoxazolyl, methylenedioxyphenyl, ethylenedioxyphenyl, naphthyridinyl, oxazolyl, phenanthridinyl, phthalazinyl, pteridinyl, purinyl, pyrazinyl, pyrazolyl, pyridazinyl, pyrazolo[3,4-b]pyridyl, pyridyl, pyrimidinyl, pyrrolyl, tetrazolyl, oxadiazolyl, thiadiazolyl, thiazolyl, thienyl, triazinyl and triazolyl.

Pyridyl, pyrazinyl, pyrimidinyl, thiazolyl, quinolinyl and thienyl are preferred.

Heterocyclyl is a 5- to 7-membered non-aromatic ring with one to three hetero atoms selected from the group comprising N, O and S.

Aromatic 5- and 6-rings are preferred, which have a nitrogen atom as hetero atom and optionally a further hetero atom, preferably nitrogen or sulphur, especially nitrogen.

Thiazolinyl and oxazolinyl are preferred.

Of the compounds of formula I, those groups are preferred in which:

(1)
- a) A is the group N=CR$_4$; or
- b) R$_1$ is methyl or ethyl, preferably methyl; or
- c) R$_2$ is methyl, ethyl, fluoromethyl or trifluoroethyl, preferably methyl; or
- d) R$_3$ is C$_1$–C$_6$-alkyl, C$_1$–C$_6$-alkoxy, C$_2$–C$_6$-alkenyl, C$_2$–C$_6$-alkenyloxy, C$_2$–C$_6$-alkynyl, C$_3$–C$_6$-alkynyloxy, C$_3$–C$_6$-cycloalkyl, C$_3$–C$_6$-cycloalkyloxy or C$_1$–C$_6$-alkoxycarbonyl, whereby the above-mentioned groups may be partially or totally halogenated; and also CN, OCN or halogen; or
- e) R$_3$ is phenyl which is unsubstituted or mono- to tri-substituted by identical or different subsituents from halogen, C$_1$–C$_6$-alkyl, C$_1$–C$_6$-halogenoalkyl, C$_1$–C$_6$-alkoxy, C$_1$–C$_6$-halogenoalkoxy, C$_2$–C$_6$-alkenyl, C$_2$–C$_6$-alkenyloxy, C$_2$–C$_6$-alkynyl, C$_3$–C$_6$-alkynyloxy, C$_1$–C$_6$-alkoxycarbonyl, CN, OCN, optionally substituted benzyl, optionally substituted phenyl or optionally substituted phenoxy, whereby the optionally substituted aromatic groups are unsubstituted or mono- to tri-substituted by identical or different subsituents from halogen, C$_1$–C$_6$-alkyl, C$_1$–C$_6$-halogenoalkyl, C$_1$–C$_6$-alkoxy, C$_1$–C$_6$-halogenoalkoxy, C$_2$–C$_6$-alkenyl, C$_2$–C$_6$-alkenyloxy, C$_2$–C$_6$-alkynyl, C$_3$–C$_6$-alkynyloxy, C$_1$–C$_6$-alkoxycarbonyl, CN or OCN; or
- f) R$_3$ is pyridyl, pyrimidinyl, furyl, thienyl, oxazolyl, isoxazolyl, thiazolyl, isothiazolyl, imidazolyl, pyrazolyl, which are unsubstituted or mono- to tri-substituted by identical or different subsituents from halogen, cyano, nitro, aminocarbonyl, C$_1$–C$_4$-alkyl, C$_1$–C$_4$-halogenoalkyl, C$_1$–C$_4$-alkylcarbonyl, C$_1$–C$_4$-alkylsulfonyl, C$_1$–C$_6$-alkylsulfoxyl, C$_3$–C$_6$-cycloalkyl, optionally substituted arylcarbonyl, C$_1$–C$_4$-alkoxy, C$_1$–C$_4$-halogenoalkoxy, C$_1$–C$_6$-alkoxycarbonyl, C$_1$–C$_6$-alkylthio, C$_1$–C$_6$-alkylamino, di-C$_1$–C$_6$-alkylamino, C$_1$–C$_6$-alkylaminocarbonyl, di-C$_1$–C$_6$-alkylaminocarbonyl or C$_2$–C$_6$-alkenyl; or
- g) R$_4$ is methyl; or
- h) R$_6$ is hydrogen.

(2) Compounds of formula I wherein:

A is N=CR$_4$;
Y is O or NH;
R$_1$ is methyl or ethyl, preferably methyl;
R$_2$ is C$_1$–C$_6$-alkyl or C$_1$–C$_6$-alkyl substituted by 1–5 fluorine atoms;
R$_3$ is C$_1$–C$_6$-alkyl, C$_1$–C$_6$-alkoxy, C$_1$–$_6$-alkoxycarbonyl, CN, C$_3$–C$_6$-cycloalkyl, aryl, heteroaryl, heterocyclyl, aryloxy, heteroaryloxy or heterocyclyloxy, whereby, with the exception of CN, the above-mentioned groups may be substituted;
R$_4$ is methyl, ethyl or cyclopropyl;
R$_6$ is hydrogen or methyl.

(2a) Of the compounds mentioned under (2), in particular those wherein:

R$_2$ is C$_1$–C$_6$-alkyl, fluoromethyl, difluoromethyl or 2,2,2-trifluoroethyl;
R$_3$ is C$_1$–C$_6$-alkyl, C$_1$–C$_6$-alkoxy, C$_1$–C$_6$-alkoxycarbonyl, CN, C$_3$–C$_6$-cycloalkyl, phenyl which is unsubstituted or mono- to tri-substituted by halogen, C$_1$–C$_4$-alkyl, C$_1$–C$_4$-halogenoalkyl, C$_1$–C$_4$-alkoxy, C$_1$–C$_4$-halogenoalkoxy, C$_2$–C$_4$-alkenyl, C$_2$–C$_4$-alkenyloxy, C$_2$–C$_6$-alkynyl, C$_3$–C$_6$-alkynyloxy, CN, OCN, benzyl, phenyl, or phenyloxy, wherein these aromatic groups are unsubstituted or mono- or di-substituted by halogen, C$_1$–C$_2$-alkyl, C$_1$–C$_2$-halogenoalkyl or C$_1$–C$_2$-alkoxy.

(2b) Of the compounds mentioned under (2a), in particular those wherein:

R$_3$ is C$_1$–C$_4$-alkyl, C$_1$–C$_4$-alkoxy, C$_1$–C$_6$-alkoxycarbonyl, or phenyl, which is unsubstituted or mono- to di-substituted by halogen, C$_1$–C$_2$-alkyl, C$_1$–C$_2$-halogenoalkyl, C$_1$–C$_2$-alkoxy.

(2c) Of the compounds mentioned under (2), in particular those wherein:

R$_3$ is C$_1$–C$_4$-alkyl, C$_1$–C$_4$-alkoxy, C$_1$–C$_6$-alkoxycarbonyl, or phenyl, which is unsubstituted or mono- to di-substituted by halogen, C$_1$–C$_2$-alkyl, C$_1$–C$_2$-halogenoalkyl, C$_1$–C$_2$-alkoxy;
R$_4$ is methyl;
R$_6$ is methyl.

(3) Compounds of formula I, wherein:

A is OCHR$_4$;
Y is O or NH;
is methyl or ethyl, preferably methyl;
R$_2$ is C$_1$–C$_6$-alkyl, preferably methyl;
R$_3$ is C$_1$–$_6$-alkyl, C$_1$–$_6$-halogenoalkyl, C$_2$–C$_6$-alkenyl, C$_1$–$_6$-alkoxy, C$_2$–C$_6$-alkenyloxy, C$_1$–C$_6$-alkoxycarbonyl, CN, C$_3$–C$_6$-cycloalkyl, aryl, heteroaryl, heterocyclyl, aryloxy, heteroaryloxy or heterocyclyloxy, whereby the hydrocarbon radicals and the cyclic radicals may be substituted as already mentioned above;
R$_4$ is methyl, ethyl or cyclopropyl, preferably methyl;
R$_6$ is hydrogen or methyl.

(3a) Of the compounds mentioned under (3), in particular those wherein:

R$_3$ is C$_1$–C$_6$-alkyl, C$_1$–C$_6$-halogenoalkyl, C$_2$–C$_6$-alkenyl, C$_1$–C$_6$-alkoxy, C$_2$–C$_6$-alkenyloxy, C$_1$–C$_6$-alkoxycarbonyl, C$_3$–C$_6$-cycloalkyl;
R$_4$ is methyl.

(3b) Of the compounds mentioned under (3), in particular those wherein:

R$_3$ is phenyl which is unsubstituted or mono- or di-substituted by halogen, C$_1$–C$_4$-alkyl, C$_1$–C$_4$-halogenoalkyl, C$_1$–C$_4$-alkoxy, C$_1$–C$_4$-halogenoalkoxy, C$_2$–C$_4$-alkenyl, C$_2$–C$_4$-alkenyloxy, benzyl, phenyl, or phenyloxy, wherein these aromatic groups are unsubstituted or mono- or di-substituted by halogen, C$_1$–C$_2$-alkyl, C$_1$–C$_2$-halogenoalkyl or C$_1$–C$_2$-alkoxy;
R$_4$ is methyl;
R$_6$ is hydrogen or methyl.

(3c) Of the compounds mentioned under (3), in particular those wherein:

$R_4$ and $R_6$ are methyl.

In EP-A-596 254 certain methoximinoacetic acid derivatives have been proposed as agricultural fungicides which are based on a benzaldoxime structure Compounds of formula I may be produced as follows:

A) A compound of formula I may be produced by reacting a compound of the general formula II

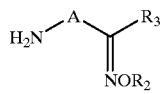

II wherein A, $R_2$ and $R_3$ have the significances given for formula I, with an aldehyde or ketone of the general formula III or with one of its acetal derivatives of the general formula IV

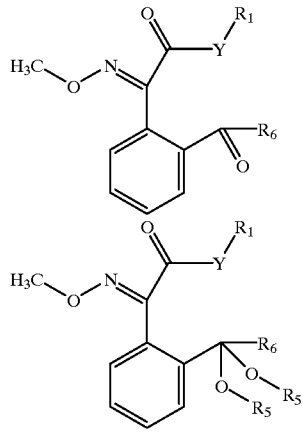

III

IV wherein Y, $R_1$ and $R_6$ have the significances given for formula I, and $R_5$ is $C_1$–$C_6$-alkyl or the two $R_5$, together with the two oxygen atoms and the carbon to which they are bonded, form a cyclic acetal.

B) A compound of formula I, wherein Y is NH and A is N=$CR_4$, may be produced by reacting a hydrazone of the general formula V,

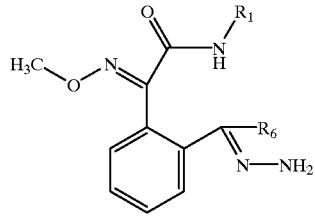

V wherein $R_1$ and $R_6$ have the significances given for formula I, with an aldehyde or a ketone of the general formula VI,

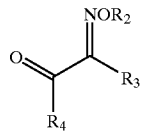

VI wherein $R_2$, $R_3$ and $R_4$ have the significances given for formula I.

C) A compound of formula I, wherein A is $OCHR_4$, may be produced by reacting an oxime of the general formula VII

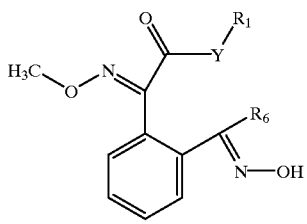

VII wherein Y, $R_1$ and $R_6$ have the significances given for formula I, with a halide of the general formula VIII

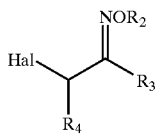

VII wherein $R_2$, $R_3$ and $R_4$ have the significances given for formula I and Hal is a halogen atom such as chlorine, bromine or iodine, especially bromine.

D) A compound of formula I may be produced whereby an oxime of the general formula IX

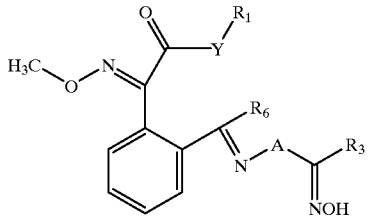

IX wherein Y, $R_1$, $R_3$, $R_6$ and A have the significances given for formula I (whereby $R_3$ cannot be halogen), is etherified.

The compounds of formula IX may be obtained whereby either a) a ketone of the general formula X

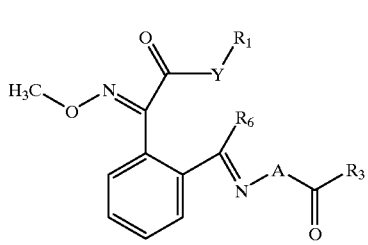

X wherein A, Y, $R_2$, $R_3$ and $R_6$ have the significances given for formula I, is reacted with hydroxylamine or with one of its salts, or b) a compound of the general formula XI

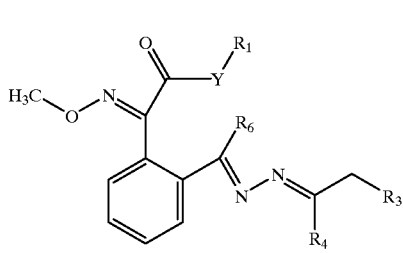

XI wherein Y, $R_1$, $R_3$, $R_4$ and $R_6$ have the significances given for formula I, is reacted with nitrous acid or with an alkyl nitrite in the presence of an acid or base, or c) an oxime of the general formula XII

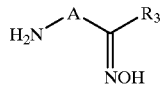

XII wherein A and $R_3$ have the significances given for formula I, is reacted with an aldehyde or ketone of the general formula III or with an acetal of the general formula IV, as described under A), or d) a ketone oxime of the general formula XIII

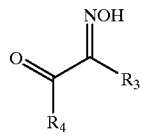

XIII wherein $R_3$ and $R_4$ have the significances given for formula I, is reacted with a hydrazone of the general formula V.

aa) A compound of formula X, wherein A is $OCHR_4$ and Y, $R_3$, $R_4$ and $R_6$ have the significances given for formula I, may be produced by reacting an oxime of formula VII with a halide of the general formula XXIV

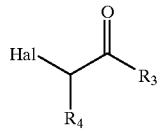

XXIV wherein Hal is a halogen atom such as chlorine, bromine or iodine, especially bromine.

E) A compound of formula I may be produced by reacting a ketone of the general formula X with an alkoxyamine of the general formula XIV

 XIV wherein $R_2$ has the significances given for formula I, or with one of its salts.

F) A compound of formula I may be produced by reacting an oxime derivative of the general formula XV

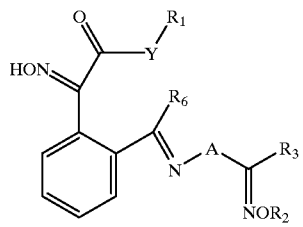

XV wherein A, Y, $R_1$, $R_2$, $R_3$ and $R_6$ have the significances given under formula I, with a methylating agent such as methyl iodide or dimethyl sulphate.

The compounds of formula XV may be obtained whereby either a) a ketone of the general formula XVI

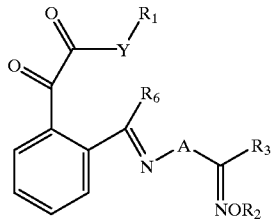

XVI wherein A, Y, $R_1$, $R_2$, $R_3$ and $R_6$ have the significances given under formula I, is reacted with hydroxylamine or with one of its salts, or b) a phenylacetic acid derivative of the general formula XVII

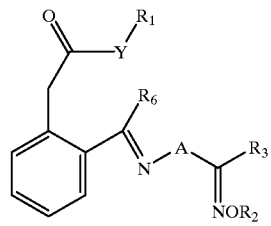

XVII wherein A, Y, $R_1$, $R_2$, $R_3$ and $R_6$ have the significances given under formula I, is reacted with nitrous acid or with an alkyl nitrite.

c) A keto derivative of the general formula XVI, wherein Y is O, may be produced whereby an acyl cyanide of the general formula XVIII

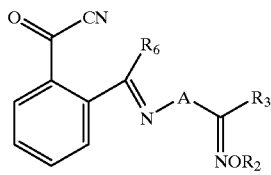

XVIII wherein A, $R_2$, $R_3$ and $R_6$ have the significances given under formula I, is reacted in a Pinner reaction with an alcohol of the general formula XIX

 XIX wherein $R_1$ has the significances given under formula I.

d) A keto derivative of the general formula XVI, wherein Y is NH, may be produced whereby either 1) a keto derivative of the general formula XVI, wherein Y is O, is reacted with an alkylamine of the general formula XX

 XX wherein $R_1$ has the significances given under formula I, or 2) an acid chloride of the general formula XXI

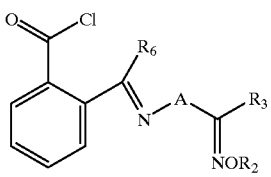

XXI wherein A, $R_2$, $R_3$ and $R_6$ have the significances given under formula I, is reacted with an isocyanide of the general formula XXII $R_1$—NC  XXII wherein $R_1$ has the significances given under formula I (see EP 547825).

G) A compound of formula I may be produced by reacting a ketone of the general formula XVI, wherein A, Y, $R_1$, $R_2$, $R_3$ and $R_6$ have the significances given under formula I, with O-methylhydroxylamine or with one of its salts.

H) A compound of formula I, wherein Y is NH, may be produced by reacting an ester of the general formula I, wherein Y is O, with an alkylamine of the general formula XX $R_1$—$NH_2$  XX wherein $R_1$ has the significances given under formula I.

I) A compound of formula I, wherein Y is NH, may be produced by reacting an oxime ether of the general formula XXIII in the presence of a ruthenium catalyst

XXIII

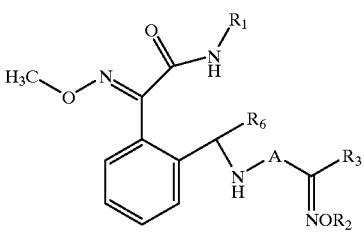

wherein A, $R_1$, $R_2$, $R_3$ and $R_6$ have the significances given under formula I, with an oxidation agent, for example dimethyl sulphoxide/oxalyl chloride, iodosobenzene, optionally in the presence of a ruthenium catalyst, potassium permanganate, manganese dioxide, tert.-butyl hypochlorite, sodium hypochlorite, tert.-butyl hydroperoxide, N-methylmorpholine-N-oxide.

All the above-described reactions are known per se, for example from WO 96/38408 and EP-A-547.825.

The above-mentioned new intermediates were developed especially for the present invention and similarly form an object of this invention; those of formulae V, IX, X, XV, XVI, XVII, XVIII, XXI and XXIII are of particular importance.

The educts are known or may be produced by known methods.

The compounds of formula I may be used preventatively and/or curatively in the agrarian sector and related fields as active ingredients for controlling plant pests. The active ingredients of formula I according to the invention are notable for their good activity even at low concentrations, for their good plant tolerance and for their environmentally friendly nature. They have very advantageous, especially systemic, properties and may be used to protect a plurality of cultivated plants. Using the active ingredients of formula I on plants or plant parts (fruit, flowers, leaves, stems, tubers, roots) of various crops, the pests appearing can be controlled or destroyed, whereby the parts of plants which grow later also remain protected, e.g. from phytopathogenic microorganisms.

The compounds I may additionally be used as a dressing to treat seeds (fruits, tubers, corms) and plant cuttings to protect against fungal infections and against phytopathogenic fungi occurring in the soil.

The compounds I are effective for example against the following classes of related phytopathogenic fungi: Fungi imperfecti (e.g. Botrytis, Pyricularia, Helminthosporium, Fusarium, Septoria, Cercospora and Alternaria); Basidiomycetes (e.g. Rhizoctonia, Hemileia, Puccinia); Ascomycetes (e.g. Venturia and Erysiphe, Podosphaera, Monilinia, Uncinula) and Oomycetes (e.g. Phytophthora, Pythium, Plasmopara).

Target crops for the plant-protecting usage in terms of the invention are for example the following plant cultivars: cereals (wheat, barley, rye, oats, rice, maize, sorghum and related species); beet (sugar beet and fodder beet); pome, stone and berry fruit (apples, pears, plums, peaches, almonds, cherries, strawberries, raspberries and blackberries); legumes (beans, lentils, peas, soya); oil crops (rape, mustard, poppy, olives, sunflowers, coconut, castor oil, cocoa, peanut); cucumber plants (squashes, cucumber, melons); fibre plants (cotton, flax, hemp, jute); citrus fruits (oranges, lemons, grapefruits, mandarines); vegetables (spinach, lettuce, asparagus, cabbage varieties, carrots, onions, tomatoes, potatoes, paprika); laurels (avocado, cinnamonium, camphor) and plants such as tobacco, nuts, coffee, aubergines, sugar cane, tea, pepper, vines, hops, bananas and natural rubber plants, as well as ornamental plants.

In addition, the compounds of formula I according to the invention are valuable active ingredients against insects and pests of the order Acarina, as are present on crop plants and ornamentals in agriculture and in horticulture and in woodland, whilst being tolerated by mammals, fish and plants. The compounds of formula I are especially suitable for the control of pests in crops of cotton, vegetables, fruit and rice, for example spider mites, aphids, caterpillars and plant- and leaf-hoppers in rice. The pests primarily controlled are spider mites such as *Panonychus ulmi,* aphids such as *Aphis craccivora,* caterpillars such as those of *Heliothis virescens* and plant- and leaf-hoppers in rice such as *Nilaparvata lugens* or *Nephotettix cincticeps.*

The good pesticidal activity of the compounds I according to the invention corresponds to a mortality of at least 50–60% of the pests mentioned.

Further areas of application for the active ingredients according to the invention are the protection of stores and material, where the storage matter is protected against putrescence and mould, as well as against insect pests (e.g. corn weevils, mites, maggots etc.). In the hygiene sector, compounds of formula I successfully control animal parasites such as ticks, mites, warble flies etc. on domestic and farm animals. The compounds I are effective against individual or collective stages of development of normally sensitive, but also resistant species of pest. Their activity may be demonstrated in this case for example by the mortality of pests which appear directly or only after some time, for example during moulting, or by reduced oviposition and/or hatching rate.

The compounds I are used in unchanged form or preferably together with customary excipients in formulation techniques. To this end, they are conveniently processed in known manner e.g. into emulsion concentrates, coatable pastes, directly sprayable or diluable solutions, diluted emulsions, wettable poweders, soluble powders, dusts or granules, e.g. by encapsulation into for example polymeric materials. As with the type of medium, the application processes, such as spraying, atomizing, dusting, scattering, coating or pouring are similarly chosen according to the desired aims and the prevailing conditions.

Suitable substrates and additives may be solid or liquid and are useful substances in formulation techniques, e.g. natural or regenerated mineral substances, dissolving aids, dispersants, wetting agents, tackifiers, thickeners, binding agents or fertilizers.

The compounds of formula I may be mixed with further active ingredients, e.g. fertilizers, ingredients providing trace elements or other plant protection compositions, especially further fungicides. In doing so, unexpected synergistic effects may occur.

Preferred additions to the mixture are:

Azoles, such as azaconazole, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, tebuconazole, tetraconazole, triadimefon, triadimenol, triflumizole, triticonazole;

pyrimidinyl carbinole, such as ancymidol, fenarimol, nuarimol;

2-amino-pyrimidines, such as bupirimate, dimethirimol, ethirimol;

morpholines, such as dodemorph, fenpropidine, fenpropimorph, spiroxamin, tridemorph;

anilinopyrimidines, such as cyprodinil, mepanipyrim, pyrimethanil;

pyrroles, such as fenpiclonil, fludioxonil;

phenylamides, such as benalaxyl, furalaxyl, metalaxyl, r-metalaxyl, ofurace, oxadixyl;

benzimidazoles, such as benomyl, carbendazim, debacarb, fuberidazole, thiabendazole;

dicarboximides, such as chlozolinate, dichlozoline, iprodione, myclozoline, procymidone, vinclozoline;

carboxamides, such as carboxin, fenfuram, flutolanil, mepronil, oxycarboxin, thifluzamide;

guanidines, such as guazatine, dodine, iminoctadine;

strobilurines, such as azoxystrobin, kresoxim-methyl, metominostrobin, SSF-129, trifloxystrobin;

dithiocarbamates, such as ferbam, mancozeb, maneb, metiram, propineb, thiram, zineb, ziram;

N-halomethylthio, such as captafol, captan, dichlofluanid, fluoromides, folpet, tolyfluanid;

Cu compounds, such as Bordeaux mixture, copper hydroxide, copper oxychloride, copper sulfate, cuprous oxide, mancopper, oxine-copper;

nitrophenol-derivatives, such as dinocap, nitrothalisopropyl;

organo-p-derivatives, such as edifenphos, iprobenphos, isoprothiolane, phosdiphen, pyrazophos, toiclofos-methyl;

Various others, such as acibenzolar-S-methyl, anilazine, blasticidin-S, chinomethionate, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, iprovalicarb, IKF-916, kasugamycin, methasulfocarb, pencycuron, phthalide, polyoxins, probenazole, propamocarb, pyroquilon, quinoxyfen, quintozene, sulfur, triaxoxide, tricyclazole, triforine, validamycin.

One preferred method of application of an active ingredient of formula I or of an agrochemical composition containing at least one of these active ingredients is foliar application. The frequency and amount of application depend on the severity of the attack by the pathogen in question. However, the active ingredients I may also reach the plants through the root system via the soil (systemic action) by drenching the locus of the plant with a liquid preparation or by incorporating the substances into the soil in solid form, e.g. in the form of granules (soil application). In rice cultivations, these granules may be dispensed over the flooded paddy field. The compounds I may however also be applied to seed grain to treat seed material (coating), whereby the grains or tubers are either drenched in a liquid preparation of the active ingredient or coated with a solid preparation.

The compositions are produced in known manner, e.g. by intimately mixing and/or grinding the active ingredient with extenders such as solvents, solid carriers and optionally surfactants.

The agrochemical compositions normally contain 0.1 to 99 percent by weight, especially 0.1 to 95 percent by weight, of active ingredient of formula I, 99.9 to 1 percent by weight, especially 99.8 to 5 percent by weight, of a solid or liquid additive and 0 to 25 percent by weight, especially 0.1 to 25 percent by weight, of a surfactant.

Favourable application rates are in general 1 g to 2 kg of active substance (AS) per hectare (ha), preferably 10 g to 1 kg AS/ha, especially 20 g to 600 g AS/ha. For usage as a seed dressing, it is advantageous to use dosages of 10 mg to 1 g active substance per kg of seed grain.

While concentrated compositions are preferred for commercial usage, the end user normally uses diluted compositions.

The compositions may also contain further additives, such as stabilizers, anti-foaming agents, viscosity regulators, binding agents or tackifiers, as well as fertilizers or other active ingredients to achieve special effects.

PREPARATION EXAMPLES

1) Methoxyimino-{2-[(2-methoxyimino-1-methyl-propylidene)-hydrazonomethylphenyl}-acetic acid methyl ester A solution of 8.85 g of (2-formylphenyl)-methoximino-acetic acid methyl ester (EP 621277) and 4.61 g of 3-hydrazono-butan-2-one oxime (Polyhedron 4, 1761, 1985) in 40 ml of pyridine is stirred for 4½ hours at a bath temperature of 100° C. After cooling, the reaction solution is poured onto ice water, and the precipitated oil is extracted with ethyl acetate. Purification takes place with ethyl acetate/hexane (1:2) on silica gel and in this way 9.4 g of {2-[(2-hydroxyimino-1-methyl-propylidene)-hydrazonomethyl]-phenyl}-methoximino-acetic acid methyl ester are obtained as slightly yellow crystals having a melting point of 148–149° C. 2.5 g of the above substance, dissolved in 15 ml of dimethylformamide, are added dropwise at 10–20° C. to a suspension of 0.44 g of sodium hydride (as a 60% dispersion in mineral oil) in 25 ml of dimethylformamide. After stirring for 15 minutes, 0.64 ml of methyl iodide are added at 10° C. and then heated to 40° C. over the course of half an hour. The reaction mixture is poured onto ice, mixed with saturated ammonium chloride solution and extracted with ethyl acetate. After drying and concentrating by evaporation, the title compound is obtained in the form of yellow crystals having a melting point of 118–119° C.

2) (2-{[2-(4-chlorophenyl)-2-methoxyimino-1-methyl-ethylidene]-hydrazonomethyl}-phenyl)-methoxyimino-acetic acid methyl ester A solution of 6.12 g of 1-(4-chlorophenyl)-propane-1,2-dione-1-(O-methyloxime) in 20 ml of ethanol is mixed with 4 ml of hydrazine hydrate. After stirring for 21 hours at room temperature, 80 ml of hexane are added. The precipitated crystals are filtered off, washed with a little hexane and dried. In this way, 4.5 g of 1-(4-chlorophenyl)-2-hydrazono-propan-1-one O-methyloxime are obtained as white crystals having a melting point of 118–119° C. A solution of 3.06 g of the above substance and 3.0 g of (2-formylphenyl)-methoxyimino-acetic acid methyl ester (EP 621277) in 30 ml of pyridine is stirred for 18 hours at 90° C. After cooling, the reaction solution is poured onto ice water and the precipitated oil is extracted with ethyl acetate. Purification takes place with ethyl acetate/hexane (1:9) on silica gel, and the title compound is obtained as a viscous, yellow oil, which crystallises after some time. (melting point 104–105° C.).

3) Methoxyimino-(2-{[2-methoxyimino-2-(4-methoxy-phenyl)-1-methyl-ethoxyimino]-methyl}-phenyl)-acetic acid methyl ester 4.84 g of finely ground potassium carbonate are added to a solution of 5.91 g of [2-(hydroxyiminomethyl)phenyl]-methoxyimino-acetic acid methyl ester (EP 499823) and 6.08 g of 2-bromo-1-(4-methoxyphenyl)-propan-1-one, and the suspension is stirred over night at room temperature. The reaction mixture is poured onto water and extracted with ethyl acetate. After purification on silica gel using ethyl acetate/hexane (3:7), 9.7 g of methoxyimino-(2-{[2-(4-methoxyphenyl)-1-methyl-2-oxo-ethoxyimino]-methyl}-phenyl)-acetic acid methyl ester are obtained as a colourless resin.

A solution of 6.0 g of the above substance and 1.67 g of 0-methylhydroxylamine hydrochloride in 30 ml of ethanol is mixed with 1.42 g of pyridine and stirred for 22 hours at room temperature. After adding water, extraction takes place with ethyl acetate, and purification is effected by means of chromatography on silica gel using ethyl acetate/hexane (3:7). 6.0 g of the title compound are thus obtained in the form of a colourless resin.

4) 2-methoxyimino-2-(2-{[methoxyimino-2-(4-methoxy-phenyl)-1-methyl-ethoxyimino]-methyl}-phenyl)-.N.-methyl-acetamide a) A solution of 4.27 g of the ester obtained under 3) in 25 ml of ethanolic methylamine (8.03 molar) is stirred over night at room temperature. After distilling off the excess methylamine and the solvent, 4.0 g of the title compound are obtained in the form of a slightly yellow resin.

b) A solution of 3.0 g of the intermediate obtained under 3) in 20 ml of ethanolic methylamine (8.03 molar) is stirred over night at room temperature. After distilling off the excess methylamine and the solvent and purifying the residue using ethyl acetate/hexane (2:3) on silica gel, 2.0 g of 2-methoxyimino-2-(2-{[2-(4-methoxy-phenyl)-1-methyl-2-oxo-ethoxyimino]-methyl}-phenyl)-.N.-methyl-acetamide are obtained as a yellowish resin.

A solution of 2 g of the above substance and 0.6 g of O-methylhydroxylamine hydrochloride in 10 ml of ethanol is mixed with 0.5 g of pyridine and stirred for 22 hours at 70° C. After adding water, extraction takes place with ethyl acetate, and purification is effected with ethyl acetate/hexane (2:3) on silica gel to give 1.8 g of the title compound in the form of a slightly yellow resin.

The compounds of the following tables can be produced in analogous manner.

TABLE 1

Compounds of the general formula I.1, in which $R_1$ and $R_2$ are methyl and $R_6$ is hydrogen, and $R_3$ corresponds in each case to one of the lines of Table A.

I.1

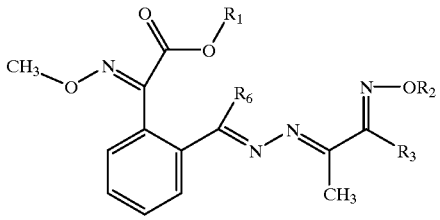

Table 2
Compounds of the general formula I.1, in which $R_1$ is ethyl, $R_2$ is methyl and $R_6$ is hydrogen, and $R_3$ corresponds in each case to one of the lines of Table A.

Table 3
Compounds of the general formula I.1, in which $R_1$ is methyl, $R_2$ is ethyl and $R_6$ is hydrogen, and $R_3$ corresponds in each case to one of the lines of Table A.

Table 4
Compounds of the general formula I.1, in which $R_1$ and $R_2$ are ethyl and $R_6$ is hydrogen, and $R_3$ corresponds in each case to one of the lines of Table A.

Table 5
Compounds of the general formula I.1, in which $R_1$; $R_2$ and $R_6$ are methyl, and $R_3$ corresponds in each case to one of the lines of Table A.

Table 6
Compounds of the general formula I.1, in which $R_1$ is ethyl, $R_2$ and $R_6$ are methyl, and $R_3$ corresponds in each case to one of the lines of Table A.

Table 7
Compounds of the general formula I.1, in which $R_1$ is methyl, $R_2$ is ethyl and $R_6$ is methyl, and $R_3$ corresponds in each case to one of the lines of Table A.

Table 8
Compounds of the general formula I.1, in which $R_1$ and $R_2$ are ethyl and $R_6$ is methyl, and $R_3$ corresponds in each case to one of the lines of Table A.

TABLE 9

Compounds of the general formula I.2, in which $R_1$ and $R_2$ are methyl and $R_6$ is hydrogen, and $R_3$ corresponds in each case to one of the lines of Table A.

I.2

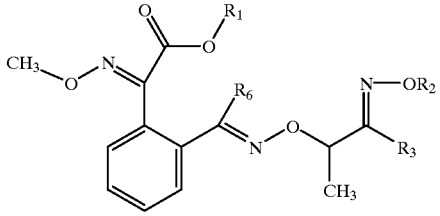

Table 10
Compounds of the general formula I.2, in which $R_1$ is ethyl, $R_2$ is methyl and $R_6$ is hydrogen, and $R_3$ corresponds in each case to one of the lines of Table A.

Table 11
Compounds of the general formula I.2, in which $R_1$ is methyl, $R_2$ is ethyl and $R_6$ is hydrogen, and $R_3$ corresponds in each case to one of the lines of Table A.

Table 12
Compounds of the general formula I.2, in which $R_1$ and $R_2$ are ethyl and $R_6$ is hydrogen, and $R_3$ corresponds in each case to one of the lines of Table A.
Table 13
Compounds of the general formula I.2, in which $R_1$, $R_2$ and $R_6$ are methyl, and $R_3$ corresponds in each case to one of the lines of Table A.
Table 14
Compounds of the general formula I.2, in which $R_1$ is ethyl, $R_2$ and $R_6$ are methyl, and $R_3$ corresponds in each case to one of the lines of Table A.
Table 15
Compounds of the general formula I.2, in which $R_1$ is methyl, $R_2$ is ethyl and $R_6$ is methyl, and $R_3$ corresponds in each case to one of the lines of Table A.
Table 16
Compounds of the general formula I.2, in which $R_1$ and $R_2$ are ethyl and $R_6$ is methyl, and $R_3$ corresponds in each case to one of the lines of Table A.

TABLE 17

Compounds of the general formula I.3, in which $R_1$ and $R_2$ are methyl and $R_6$ is hydrogen, and $R_3$ corresponds in each case to one of the lines of Table A.

I.3

Table 18
Compounds of the general formula I.3, in which $R_1$ is methyl, $R_2$ is ethyl and $R_6$ is hydrogen, and $R_3$ corresponds in each case to one of the lines of Table A.
Table 19
Compounds of the general formula I.3, in which $R_1$, $R_2$ and $R_6$ are methyl, and $R_3$ corresponds in each case to one of the lines of Table A.
Table 20
Compounds of the general formula I.3, in which $R_1$ is methyl, $R_2$ is ethyl and $R_6$ is methyl, and $R_3$ corresponds in each case to one of the lines of Table A.

TABLE 21

Compounds of the general formula I.4, in which $R_1$ and $R_2$ are methyl and $R_6$ is hydrogen, and $R_3$ corresponds in each case to one of the lines of Table A.

I.4

Table 22
Compounds of the general formula I.4, in which $R_1$ is methyl, $R_2$ is ethyl and $R_6$ is hydrogen, and $R_3$ corresponds in each case to one of the lines of Table A.
Table 23
Compounds of the general formula I.4, in which $R_1$, $R_2$ and $R_6$ are methyl, and $R_3$ corresponds in each case to one of the lines of Table A.
Table 24
Compounds of the general formula I.4, in which $R_1$ is methyl, $R_2$ is ethyl and $R_6$ is methyl, and $R_3$ corresponds in each case to one of the lines of Table A.
Table 25
Compounds of the general formula I.1, in which $R_1$ is methyl, $R_2$ is fluoromethyl and $R_6$ is hydrogen, and $R_3$ corresponds in each case to one of the lines of Table A.
Table 26
Compounds of the general formula I.1, in which $R_1$ is methyl, $R_2$ is difluoromethyl and $R_6$ is hydrogen, and $R_3$ corresponds in each case to one of the lines of Table A.
Table 27
Compounds of the general formula I.1, in which $R_1$ is methyl, $R_2$ is 2,2,2-trifluoroethyl and $R_6$ is hydrogen, and $R_3$ corresponds in each case to one of the lines of Table A.
Table 28
Compounds of the general formula I.1, in which $R_1$ is ethyl, $R_2$ is fluoromethyl and $R_6$ is hydrogen, and $R_3$ corresponds in each case to one of the lines of Table A.
Table 29
Compounds of the general formula I.1, in which $R_1$ is ethyl, $R_2$ is difluoromethyl and $R_6$ is hydrogen, and $R_3$ corresponds in each case to one of the lines of Table A.
Table 30
Compounds of the general formula I.1, in which $R_1$ is ethyl, $R_2$ is 2,2,2-trifluoroethyl and $R_6$ is hydrogen, and $R_3$ corresponds in each case to one of the lines of Table A.
Table 31
Compounds of the general formula I.1, in which $R_1$ is methyl, $R_2$ is fluoromethyl and $R_6$ is methyl, and $R_3$ corresponds in each case to one of the lines of Table A.
Table 32
Compounds of the general formula I.1, in which $R_1$ is methyl, $R_2$ is difluoromethyl and $R_6$ is methyl, and $R_3$ corresponds in each case to one of the lines of Table A.
Table 33
Compounds of the general formula I.1, in which $R_1$ is methyl, $R_2$ is 2,2,2-trifluoroethyl and $R_6$ is methyl, and $R_3$ corresponds in each case to one of the lines of Table A.
Table 34
Compounds of the general formula I.1, in which $R_1$ is ethyl, $R_2$ is fluoromethyl and $R_6$ is methyl, and $R_3$ corresponds in each case to one of the lines of Table A.
Table 35
Compounds of the general formula I.1, in which $R_1$ is ethyl, $R_2$ is difluoromethyl and $R_6$ is methyl, and $R_3$ corresponds in each case to one of the lines of Table A.
Table 36
Compounds of the general formula I.1, in which $R_1$ is ethyl, $R_2$ is 2,2,2-trifluoroethyl and $R_6$ is methyl, and $R_3$ corresponds in each case to one of the lines of Table A.
Table 37
Compounds of the general formula I.3, in which $R_1$ is methyl, $R_2$ is fluoromethyl and $R_6$ is hydrogen, and $R_3$ corresponds in each case to one of the lines of Table A.
Table 38
Compounds of the general formula I.3, in which $R_1$ is methyl, $R_2$ is difluoromethyl and $R_6$ is hydrogen, and $R_3$ corresponds in each case to one of the lines of Table A.
Table 39
Compounds of the general formula I.3, in which $R_1$ is methyl, $R_2$ is 2,2,2-trifluoroethyl and $R_6$ is hydrogen, and $R_3$ corresponds in each case to one of the lines of Table A.

Table 40

Compounds of the general formula I.3, in which $R_1$ is methyl, $R_2$ is fluoromethyl and $R_6$ is methyl, and $R_3$ corresponds in each case to one of the lines of Table A.

Table 41

Compounds of the general formula I.3, in which $R_1$ is methyl, $R_2$ is difluoromethyl and $R_6$ is methyl, and $R_3$ corresponds in each case to one of the lines of Table A.

Table 42

Compounds of the general formula I.3, in which $R_1$ is methyl, $R_2$ is 2,2,2-trifluoroethyl and $R_6$ is methyl, and $R_3$ corresponds in each case to one of the lines of Table A.

TABLE 43

Compounds of the general formula I.5, in which $R_1$ and $R_2$ are methyl and $R_6$ is hydrogen, and $R_3$ corresponds in each case to one of the lines of Table A.

I.5

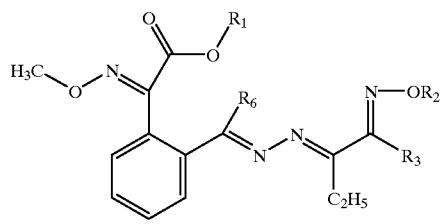

Table 44

Compounds of the general formula I.5, in which $R_1$ is ethyl, $R_2$ is methyl and $R_6$ is hydrogen, and $R_3$ corresponds in each case to one of the lines of Table A.

Table 45

Compounds of the general formula I.5, in which $R_1$, $R_2$ and $R_6$ are methyl, and $R_3$ corresponds in each case to one of the lines of Table A.

Table 46

Compounds of the general formula I.5, in which $R_1$ is ethyl, $R_2$ and $R_6$ are methyl, and $R_3$ corresponds in each case to one of the lines of Table A.

TABLE 47

Compounds of the general formula I.6, in which $R_1$ and $R_2$ are methyl and $R_6$ is hydrogen, and $R_3$ corresponds in each case to one of the lines of Table A.

I.6

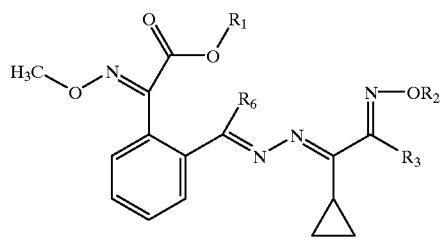

Table 48

Compounds of the general formula I.6, in which $R_1$ is ethyl, $R_2$ is methyl and $R_6$ is hydrogen, and $R_3$ corresponds in each case to one of the lines of Table A.

Table 49

Compounds of the general formula I.6, in which $R_1$, $R_2$ and $R_6$ are methyl, and $R_3$ corresponds in each case to one of the lines of Table A.

Table 50

Compounds of the general formula I.6, in which $R_1$ is ethyl, $R_2$ and $R_6$ are methyl, and $R_3$ corresponds in each case to one of the lines of Table A.

TABLE 51

Compounds of the general formula I.7, in which $R_1$ and $R_2$ are methyl and $R_6$ is hydrogen, and $R_3$ corresponds in each case to one of the lines of Table A.

I.7

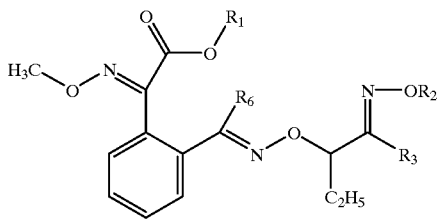

Table 52

Compounds of the general formula I.7, in which $R_1$ is ethyl, $R_2$ is methyl and $R_6$ is hydrogen, and $R_3$ corresponds in each case to one of the lines of Table A.

Table 53

Compounds of the general formula I.7, in which $R_1$, $R_2$ and $R_6$ are methyl, and $R_3$ corresponds in each case to one of the lines of Table A.

Table 54

Compounds of the general formula I.7, in which $R_1$ is ethyl, $R_2$ and $R_6$ are methyl, and $R_3$ corresponds in each case to one of the lines of Table A.

TABLE 55

Compounds of the general formula I.8, in which $R_1$ and $R_2$ are methyl and $R_6$ is hydrogen, and $R_3$ corresponds in each case to one of the lines of Table A.

I.8

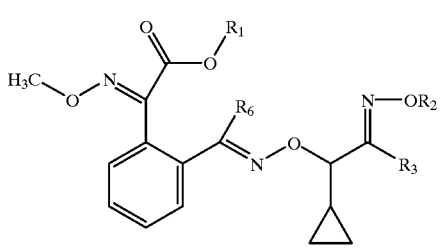

Table 56

Compounds of the general formula I.8, in which $R_1$ is ethyl, $R_2$ is methyl and $R_6$ is hydrogen, and $R_3$ corresponds in each case to one of the lines of Table A.

Table 57

Compounds of the general formula I.8, in which $R_1$, $R_2$ and $R_6$ are methyl, and $R_3$ corresponds in each case to one of the lines of Table A.

Table 58

Compounds of the general formula I.8, in which $R_1$ is ethyl, $R_2$ and $R_6$ are methyl, and $R_3$ corresponds in each case to one of the lines of Table A.

TABLE 59

Compounds of the general formula I.9, in which $R_1$ and $R_2$ are methyl and $R_6$ is hydrogen, and $R_3$ corresponds in each case to one of the lines of Table A.

I.9

Table 60

Compounds of the general formula I.9, in which $R_1$, $R_2$ and $R_6$ are methyl, and $R_3$ corresponds in each case to one of the lines of Table A.

TABLE 61

Compounds of the general formula I.10, in which $R_1$ and $R_2$ are methyl and $R_6$ is hydrogen, and $R_3$ corresponds in each case to one of the lines of Table A.

I.10

Table 62

Compounds of the general formula I.1 0, in which $R_1$, $R_2$ and $R_6$ are methyl, and $R_3$ corresponds in each case to one of the lines of Table A.

TABLE 63

Compounds of the general formula I.11, in which $R_1$ and $R_2$ are methyl and $R_6$ is hydrogen, and $R_3$ corresponds in each case to one of the lines of Table A.

I.11

Table 64

Compounds of the general formula I.11, in which $R_1$, $R_2$ and $R_6$ are methyl, and $R_3$ corresponds in each case to one of the lines of Table A.

TABLE 65

Compounds of the general formula I.12, in which $R_1$ and $R_2$ are methyl and $R_6$ is hydrogen, and $R_3$ corresponds in each case to one of the lines of Table A.

I.12

Table 66

Compounds of the general formula I.12, in which $R_1$, $R_2$ and $R_6$ are methyl, and $R_3$ corresponds in each case to one of the lines of Table A.

TABLE A

| No. | $R_3$ |
|---|---|
| 1. | $CH_3$ |
| 2. | $CH_2CH_3$ |
| 3. | $(CH_2)_2CH_3$ |
| 4. | $(CH_2)_3CH_3$ |
| 5. | $(CH_2)_4CH_3$ |
| 6. | $(CH_2)_5CH_3$ |
| 7. | $CH(CH_3)_2$ |
| 8. | $C(CH_3)_3$ |
| 9. | $CH_2CH(CH_3)_2$ |
| 10. | $CH(CH_3)CH_2CH_3$ |
| 11. | $OCH_3$ |
| 12. | $OCH_2CH_3$ |
| 13. | $O(CH_2)_2CH_3$ |
| 14. | $O(CH_2)_3CH_3$ |
| 15. | $O(CH_2)_4CH_3$ |
| 16. | $OCH(CH_3)_2$ |
| 17. | $OCH(CH_3)CH_2CH_3$ |
| 18. | $OC(CH_3)_3$ |
| 19. | $CH=CH_2$ |
| 20. | $CH=CHCH_3$ |
| 21. | $CH=C(CH_3)_2$ |
| 22. | $CH_2CH=CH_2$ |
| 23. | $CH_2CH=CHCH_3$ |
| 24. | $OCH_2CH=CH_2$ |
| 25. | $C\equiv CH$ |
| 26. | $C\equiv CCH_3$ |
| 27. | $C\equiv CC(CH_3)_3$ |
| 28. | $CH_2C\equiv CH$ |
| 29. | $CH_2C\equiv CH_3$ |
| 30. | $OCH_2C\equiv CH_3$ |
| 31. | $OCH_2C\equiv C-C(CH_3)_3$ |
| 32. | $C(O)OCH_3$ |
| 33. | $C(O)OCH_2CH_3$ |
| 34. | $C(O)O(CH_2)_2CH_3$ |
| 35. | $C(O)O(CH_2)_3CH_3$ |
| 36. | $C(O)O(CH_2)_4CH_3$ |
| 37. | $C(O)OCH(CH_3)_2$ |
| 38. | $C(O)OC(CH_3)_3$ |
| 39. | CN |
| 40. | Cl |
| 41. | Br |
| 42. | $CF_3$ |
| 43. | $CH_2CF_3$ |
| 44. | $CH_2CH_2F$ |
| 45. | $CH_2CN$ |
| 46. | $CH_2OCH_3$ |
| 47. | $CH_2OCH_2CH_3$ |
| 48. | $(CH_2)_2COOCH_3$ |
| 49. | $(CH_2)_2CONH_2$ |
| 50. | $(CH_2)_2CONHCH_3$ |
| 51. | $(CH_2)_2CON(CH_3)_2$ |

TABLE A-continued

| No. | R₃ |
|---|---|
| 52. | (CH$_2$)$_2$SCH$_3$ |
| 53. | CH$_2$OCH$_2$CH=CH$_2$ |
| 54. | CH$_2$—⊲ (cyclopropyl) |
| 55. | CH$_2$O—cyclohexyl |
| 56. | CH=CF$_2$ |
| 57. | C≡C—Br |
| 58. | C≡C—OCH$_3$ |
| 59. | Cyclopropyl |
| 60. | Cyclobutyl |
| 61. | Cyclopentyl |
| 62. | Cyclohexyl |
| 63. | Phenyl |
| 64. | 1-Naphthyl |
| 65. | 2-Naphthyl |
| 66. | 2-F—C$_6$H$_4$ |
| 67. | 3-F—C$_6$H$_4$ |
| 68. | 4-F—C$_6$H$_4$ |
| 69. | 2,3-F$_2$—C$_6$H$_3$ |
| 70. | 2,4-F$_2$—C$_6$H$_3$ |
| 71. | 2,5-F$_2$—C$_6$H$_3$ |
| 72. | 2,6-F$_2$—C$_6$H$_3$ |
| 73. | 3,4-F$_2$—C$_6$H$_3$ |
| 74. | 3,5-F$_2$—C$_6$H$_3$ |
| 75. | 2-Cl—C$_6$H$_4$ |
| 76. | 3-Cl—C$_6$H$_4$ |
| 77. | 4-Cl—C$_6$H$_4$ |
| 78. | 2,3-Cl$_2$—C$_6$H$_3$ |
| 79. | 2,4-Cl$_2$—C$_6$H$_3$ |
| 80. | 2,5-Cl$_2$—C$_6$H$_3$ |
| 81. | 2,6-Cl$_2$—C$_6$H$_3$ |
| 82. | 3,4-Cl$_2$—C$_6$H$_3$ |
| 83. | 3,5-Cl$_2$—C$_6$H$_3$ |
| 84. | 2,3,4-Cl$_3$—C$_6$H$_2$ |
| 85. | 2,3,5-Cl$_3$—C$_6$H$_2$ |
| 86. | 2,3,6-Cl$_3$—C$_6$H$_2$ |
| 87. | 2,4,5-Cl$_3$—C$_6$H$_2$ |
| 88. | 2,4,6-Cl$_3$—C$_6$H$_2$ |
| 89. | 3,4,5-Cl$_3$—C$_6$H$_2$ |
| 90. | 2-Br—C$_6$H$_4$ |
| 91. | 3-Br—C$_6$H$_4$ |
| 92. | 4-Br—C$_6$H$_4$ |
| 93. | 2,3-Br$_2$—C$_6$H$_3$ |
| 94. | 2,4-Br$_2$—C$_6$H$_3$ |
| 95. | 2,5-Br$_2$—C$_6$H$_3$ |
| 96. | 2,6-Br$_2$—C$_6$H$_3$ |
| 97. | 3,4-Br$_2$—C$_6$H$_3$ |
| 98. | 3,5-Br$_2$—C$_6$H$_3$ |
| 99. | 2-F-3-Cl—C$_6$H$_3$ |
| 100. | 2-F-4-Cl—C$_6$H$_3$ |
| 101. | 2-F-5-Cl—C$_6$H$_3$ |
| 102. | 2-F-3-Br—C$_6$H$_3$ |
| 103. | 2-F-4-Br—C$_6$H$_3$ |
| 104. | 2-F-5-Br—C$_6$H$_3$ |
| 105. | 2-Cl-3-Br—C$_6$H$_3$ |
| 106. | 2-Cl-3-Br—C$_6$H$_3$ |
| 107. | 2-Cl-5-Br—C$_6$H$_3$ |
| 108. | 3-F-4-Cl—C$_6$H$_3$ |
| 109. | 3-F-5-Cl—C$_6$H$_3$ |
| 110. | 3-F-6-Cl—C$_6$H$_3$ |
| 111. | 3-F-4-Br—C$_6$H$_3$ |
| 112. | 3-F-5-Br—C$_6$H$_3$ |
| 113. | 3-F-6-Br—C$_6$H$_3$ |
| 114. | 3-Cl-4-Br—C$_6$H$_3$ |
| 115. | 3-Cl-5-Br—C$_6$H$_3$ |
| 116. | 3-Cl-6-Br—C$_6$H$_3$ |
| 117. | 4-F-5-Cl—C$_6$H$_3$ |
| 118. | 4-F-6-Cl—C$_6$H$_3$ |
| 119. | 4-F-5-Br—C$_6$H$_3$ |
| 120. | 4-F-6-Br—C$_6$H$_3$ |
| 121. | 4-Cl-5-Br—C$_6$H$_3$ |
| 122. | 5-F-6-Ci-C$_6$H$_3$ |
| 123. | 5-F-6-Br—C$_6$H$_3$ |
| 124. | 5-Cl-6-Br—C$_6$H$_3$ |
| 125. | 3-Br-4-Cl-5-Br—C$_6$H$_2$ |
| 126. | 2-CN—C$_6$H$_4$ |
| 127. | 3-CN—C$_6$H$_4$ |
| 128. | 4-CN—C$_6$H$_4$ |
| 129. | 3-OCN—C$_6$H$_4$ |
| 130. | 4-OCN—C$_6$H$_4$ |
| 131. | 2-CH$_3$O—C$_6$H$_4$ |
| 132. | 3-CH$_3$O—C$_6$H$_4$ |
| 133. | 4-CH$_3$O—C$_6$H$_4$ |
| 134. | 2,3-(CH$_3$O)$_2$—C$_6$H$_3$ |
| 135. | 2,4-(CH$_3$O)$_2$—C$_6$H$_3$ |
| 136. | 2,5-(CH$_3$O)$_2$—C$_6$H$_3$ |
| 137. | 3,4-(CH$_3$O)$_2$—C$_6$H$_3$ |
| 138. | 3,5-(CH$_3$O)$_2$—C$_6$H$_3$ |
| 139. | 3,4,5-(CH$_3$O)$_3$—C$_6$H$_2$ |
| 140. | 2-C$_2$H$_5$O—C$_6$H$_4$ |
| 141. | 3-C$_2$H$_5$O—C$_6$H$_4$ |
| 142. | 4-C$_2$H$_5$O—C$_6$H$_4$ |
| 143. | 2-(n-C$_3$H$_7$O)—C$_6$H$_4$ |
| 144. | 3-(n-C$_3$H$_7$O)—C$_6$H$_4$ |
| 145. | 4-(n-C$_3$H$_7$O)—C$_6$H$_4$ |
| 146. | 2-(i-C$_3$H$_7$O)—C$_6$H$_4$ |
| 147. | 3-(i-C$_3$H$_7$O)—C$_6$H$_4$ |
| 148. | 4-(i-C$_3$H$_7$O)—C$_6$H$_4$ |
| 149. | 4-(n-C$_4$H$_9$O)—C$_6$H$_4$ |
| 150. | 3-(t-C$_4$H$_9$O)—C$_6$H$_4$ |
| 151. | 4-(t-C$_4$H$_9$O)—C$_6$H$_4$ |
| 152. | 2-Allyl—O—C$_6$H$_4$ |
| 153. | 3-Allyl—O—C$_6$H$_4$ |
| 154. | 4-Allyl—O—C$_6$H$_4$ |
| 155. | 2-CF$_3$—C$_6$H$_4$ |
| 156. | 3-CF$_3$—C$_6$H$_4$ |
| 157. | 4-CF$_3$—C$_6$H$_4$ |
| 158. | 2-Acetyl—C$_6$H$_4$ |
| 159. | 3-Acetyl—C$_6$H$_4$ |
| 160. | 4-Acetyl—C$_4$H$_4$ |
| 161. | 2-Methoxycarbonyl—C$_6$H$_4$ |
| 162. | 3-Methoxycarbonyl—C$_6$H$_4$ |
| 163. | 4-Methoxycarbonyl—C$_6$H$_4$ |
| 164. | 2-Aminocarbonyl—C$_6$H$_4$ |
| 165. | 3-Aminocarbonyl—C$_6$H$_4$ |
| 166. | 4-Aminocarbonyl—C$_6$H$_4$ |
| 167. | 2-Dimethylaminocarbonyl—C$_6$H$_4$ |
| 168. | 3-Dimethylaminocarbonyl—C$_6$H$_4$ |
| 169. | 4-Dimethylaminocarbonyl—C$_6$H$_4$ |
| 170. | 2-(N—Methylaminocarbonyl)—C$_6$H$_4$ |
| 171. | 3-(N—Methylaminocarbonyl)—C$_6$H$_4$ |
| 172. | 4-(N—Methylaminocarbonyl)—C$_6$H$_4$ |
| 173. | 2-CH$_3$S—C$_6$H$_4$ |
| 174. | 3-CH$_3$S—C$_6$H$_4$ |
| 175. | 4-CH$_3$S—C$_6$H$_4$ |
| 176. | 2-CH$_3$SO$_2$—C$_6$H$_4$ |
| 177. | 3-CH$_3$SO$_2$—C$_6$H$_4$ |
| 178. | 4-CH$_3$SO$_2$—C$_6$H$_4$ |
| 179. | 2-CF$_3$O—C$_6$H$_4$ |
| 180. | 3-CF$_3$O—C$_6$H$_4$ |
| 181. | 4-CF$_3$O—C$_6$H$_4$ |
| 182. | 2-CHF$_2$O—C$_6$H$_4$ |
| 183. | 3-CHF$_2$O—C$_6$H$_4$ |
| 184. | 4-CHF$_2$O—C$_6$H$_4$ |
| 185. | 3-CF$_3$, 4-CF$_3$O—C$_6$H$_3$ |
| 186. | 2-CH$_3$NH—C$_6$H$_4$ |
| 187. | 3-CH$_3$NH—C$_6$H$_4$ |
| 188. | 4-CH$_3$NH—C$_6$H$_4$ |
| 189. | 2-(CH$_3$)$_2$N—C$_6$H$_4$ |
| 190. | 3-(CH$_3$)$_2$N—C$_6$H$_4$ |
| 191. | 4-(CH$_3$)$_2$N—C$_6$H$_4$ |
| 192. | 2-Ethoxycarbonyl—C$_6$H$_4$ |
| 193. | 3-Ethoxycarbonyl—C$_6$H$_4$ |
| 194. | 4-Ethoxycarbonyl—C$_6$H$_4$ |
| 195. | 2-CH$_2$FCH$_2$—C$_6$H$_4$ |
| 196. | 3-CH$_2$FCH$_2$—C$_6$H$_4$ |

TABLE A-continued

| No. | R₃ |
|---|---|
| 197. | 4-CH₂FCH₂—C₆H₄ |
| 198. | 2-CF₃CH₂—C₆H₄ |
| 199. | 3-CF₃CH₂—C₆H₄ |
| 200. | 4-CF₃CH₂—C₆H₄ |
| 201. | 2-CHF₂CF₂—C₆H₄ |
| 202. | 3-CHF₂CF₂—C₆H₄ |
| 203. | 4-CHF₂CF₂—C₆H₄ |
| 204. | 2-CHF₂—C₆H₄ |
| 205. | 3-CHF₂—C₆H₄ |
| 206. | 4-CHF₂—C₆H₄ |
| 207. | 2-NO₂—C₆H₄ |
| 208. | 3-NO₂—C₆H₄ |
| 209. | 4-NO₂—C₆H₄ |
| 210. | 2-CH₃—C₆H₄ |
| 211. | 3-CH₃—C₆H₄ |
| 212. | 4-CH₃—C₆H₄ |
| 213. | 2,3-(CH₃)₂—C₆H₃ |
| 214. | 2,4-(CH₃)₂—C₆H₃ |
| 215. | 2,5-(CH₃)₂—C₆H₃ |
| 216. | 2,6-(CH₃)₂—C₆H₃ |
| 217. | 3,4-(CH₃)₂—C₆H₃ |
| 218. | 3,5-(CH₃)₂—C₆H₃ |
| 219. | 2-C₂H₅—C₆H₄ |
| 220. | 3-C₂H₅—C₆H₄ |
| 221. | 4-C₂H₅—C₆H₄ |
| 222. | 2-i-C₃H₇—C₆H₄ |
| 223. | 3-i-C₃H₇—C₆H₄ |
| 224. | 4-i-C₃H₇—C₆H₄ |
| 225. | 3-tert.-C₄H₉—C₆H₄ |
| 226. | 4-tert.-C₄H₉—C₆H₄ |
| 227. | 2-Vinyl—C₆H₄ |
| 228. | 3-Vinyl—C₆H₄ |
| 229. | 4-Vinyl—C₆H₄ |
| 230. | 2-Allyl—C₆H₄ |
| 231. | 3-Allyl—C₆H₄ |
| 232. | 4-Allyl—C₆H₄ |
| 233. | 2-Propargyl—C₆H₄ |
| 234. | 2-Ethinyl—C₆H₄ |
| 235. | 3-Propargyloxy—C₆H₄ |
| 236. | 4-Butinyloxy—C₆H₄ |
| 237. | 2-C₆H₅—C₆H₄ |
| 238. | 3-C₆H₅—C₆H₄ |
| 239. | 4-C₆H₅—C₆H₄ |
| 240. | 3-CH₃—5-t-C₄H₉—C₆H₃ |
| 241. | 2-F-4-CH₃—C₆H₃ |
| 242. | 2-F-5-CH₃—C₆H₃ |
| 243. | 2-CH₃—4-F—C₆H₃ |
| 244. | 2-CH₃—5-F—C₆H₃ |
| 245. | 2-CH₃—4-Cl—C₆H₃ |
| 246. | 2-F-4-CH₃—O—C₆H₃ |
| 247. | 2-F-4-CH₃CH₂O—C₆H₃ |
| 248. | 2-F-4-i-C₃H₇—C₆H₃ |
| 249. | 4-(4-Chlorophenoxy)phenyl |
| 250. | 4-(4-Trifluoromethylphenoxy)phenyl |
| 251. | 4-(3-Chlorophenoxy)phenyl |
| 252. | 4-(3-Trifluoromethylphenoxy)phenyl |
| 253. | 2-Pyridyl |
| 254. | 3-Pyridyl |
| 255. | 4-Pyridyl |
| 256. | 5-CH₃—Pyridin-2-yl |
| 257. | 5-Cl—Pyridin-2-yl |
| 258. | 6-Cl—Pyridin-2-yl |
| 259. | 3,5-Cl₂—Pyridin-2-yl |
| 260. | 6-CH₃O—Pyridin-2-yl |
| 261. | 6-CH₃—Pyridin-2-yl |
| 262. | 6-Cl—Pyridin-3-yl |
| 263. | 6-CH₃—Pyridin-3-yl |
| 264. | 6-CH₃O—Pyridin-3-yl |
| 265. | 2-Pyrimidinyl |
| 266. | 4-CH₃O—Pyrimidin-2-yl |
| 267. | 4-C₂H₅O—Pyrimidin-2-yl |
| 268. | 4-Cl—Pyrimidin-2-yl |
| 269. | 4-CH₃—Pyrimidin-2-yl |
| 270. | 5-CH₃—Pyrimidin-2-yl |
| 271. | 5-Cl—Pyrimidin-2-yl |
| 272. | 5-CH₃O—Pyrimidin-2-yl |
| 273. | 5-C₂H₅O—Pyrimidin-2-yl |
| 274. | 4-Pyrimidinyl |
| 275. | 2-Cl—Pyrimidin-4-yl |
| 276. | 2-CH₃O—Pyrimidin-4-yl |
| 277. | 2-CH₃—Pyrimidin-4-yl |
| 278. | 6-Cl—Pyrimidin-4-yl |
| 279. | 6-CH₃—Pyrimidin-4-yl |
| 280. | 6-CH₃O—Pyrimidin-4-yl |
| 281. | 5-Pyrimidinyl |
| 282. | 2-CH₃—Pyrimidin-5-yl |
| 283. | 2-Cl—Pynmidin-5-yl |
| 284. | 2-CH₃O—Pyrimidin-5-yl |
| 285. | 2-C₂H₅O—Pyrimidin-5-yl |
| 286. | 2-Furyl |
| 287. | 4-C₂H₅—Fur-2-yl |
| 288. | 4-CH₃—Fur-2-yl |
| 289. | 4-Cl—Fur-2-yl |
| 290. | 4-CN—Fur-2-yl |
| 291. | 5-CH₃—Fur-2-yl |
| 292. | 5-Cl—Fur-2-yl |
| 293. | 5-CN—Fur-2-yl |
| 294. | 3-Furyl |
| 295. | 5-CH₃—Fur-3-yl |
| 296. | 5-Cl—Fur-3-yl |
| 297. | 5-CN—Fur-3-yl |
| 298. | 2-Thienyl |
| 299. | 4-CH₃—Thien-2-yl |
| 300. | 4-Cl—Thien-2-yl |
| 301. | 4-CN—Thien-2-yl |
| 302. | 5-CH₃—Thien-2-yl |
| 303. | 5-Cl—Thien-2-yl |
| 304. | 5-CN—Thien-2-yl |
| 305. | 3-Thienyl |
| 306. | 5-CH₃—Thien-3-yl |
| 307. | 5-Cl—Thien-3-yl |
| 308. | 5-CN—Thien-3-yl |
| 309. | 1-Methylpropyl-2-yl |
| 310. | 1-Methylpropyl-3-yl |
| 311. | 2-Oxazolyl |
| 312. | 4-CH₃—Oxazol-2-yl |
| 313. | 4-Cl—Oxazol-2-yl |
| 314. | 4-CN—Oxazol-2-yl |
| 315. | 5-CH₃—Oxazol-2-yl |
| 316. | 5-Cl—Oxazol-2-yl |
| 317. | 5-CN—Oxazol-2-yl |
| 318. | 4-Oxazolyl |
| 319. | 2-CH₃—Oxazol-4-yl |
| 320. | 2-Cl—Oxazol-4-yl |
| 321. | 2-CN—Oxazol-4-yl |
| 322. | 5-Oxazolyl |
| 323. | 2-CH₃—Oxazol-5-yl |
| 324. | 2-Cl—Oxazol-5-yl |
| 325. | 2-CN—Oxazol-5-yl |
| 326. | 3-isoxazolyl |
| 327. | 5-CH₃—isoxazol-3-yl |
| 328. | 5-Cl—i soxazol-3-yl |
| 329. | 5-CN—lsoxazol-3-yl |
| 330. | 5-isoxazolyl |
| 331. | 3-CH₃—isoxazol-5-.yl |
| 332. | 3-Cl—isoxazol-5-yl |
| 333. | 3-CN—isoxazol-5-yl |
| 334. | 2-Thiazolyl |
| 335. | 4-CH₃—Thiazol-2-yl |
| 336. | 4-Cl—Thiazol-2-yl |
| 337. | 4-CN—Thiazol-2-yl |
| 338. | 5-CH₃—Thiazol-2-yl |
| 339. | 5-Cl—Thiazol-2-yl |
| 340. | 5-CN—Thiazol-2-yl |
| 341. | 4-Thiazolyl |
| 342. | 2-CH₃—Thiazol-4-yl |
| 343. | 2-Cl—Thiazol-4-yl |
| 344. | 2-CN—Thiazol-4-yl |
| 345. | 2-CH₃S—Thiazol-4-yl |
| 346. | 5-Thiazolyl |
| 347. | 2-CH₃—Thiazol-5-yl |
| 348. | 2-Cl—Thiazol-5-yl |
| 349. | 2-CN—Thiazol-5-yl |
| 350. | 3-Isothiazolyl |

TABLE A-continued

| No. | R₃ |
|---|---|
| 351. | 5-CH₃—Isothiazol-3-yl |
| 352. | 5-Cl—Isothiazol-3-yl |
| 353. | 5-CN—Isothiazol-3-yl |
| 354. | 5-Isothiazolyl |
| 355. | 3-CH₃—Isothiazol-5-yl |
| 356. | 3-Cl—Isothiazol-5-yl |
| 357. | 3-CN—Isothiazol-5-yl |
| 358. | 2-Imidazolyl |
| 359. | 4-CH₃—Imidazol-2-yl |
| 360. | 4-Cl—Imidazol-2-yl |
| 361. | 4-CN—Imidazol-2-yl |
| 362. | 1-CH₃—Imidazol-2-yl |
| 363. | 1-CH₃-4-Cl—Imidazol-2-yl |
| 364. | 1,4-(CH₃)₂—Imidazol-2-yl |
| 365. | 1-CH₃—5-Cl—Imidazol-2-yl |
| 366. | 1,5-(CH₃)₂—Imidazol-2-yl |
| 367. | 4-Imidazolyl |
| 368. | 2-CH₃—Imidazol-4-yl |
| 369. | 2-Cl—Imidazol-4-yl |
| 370. | 1-CH₃—Imidazol-4-yl |
| 371. | 1,2-(CH₃)₂—Imidazol-4-yl |
| 372. | 1-CH₃—2-Cl—Imidazol-4-yl |
| 373. | 1-CH₃—Imidazol-5-yl |
| 374. | 1-CH₃—3-Cl—Imidazol-5-yl |
| 375. | 1,2-(CH₃)₂—Imidazol-5-yl |
| 376. | 3-Pyrazolyl |
| 377. | 5-CH₃—Pyrazol-3-yl |
| 378. | 5-Cl—Pyrazol-3-yl |
| 379. | 5-CN—Pyrazol-3-yl |
| 380. | 1-CH₃—Pyrazol-3-yl |
| 381. | 1-CH₃-4-Cl—Pyrazol-3-yl |
| 382. | 1-CH₃—5-Cl—Pyrazol-3-yl |
| 383. | 1,5-(CH₃)₂—Pyrazol-3-yl |
| 384. | 1-CH₃—Pyrazol-5-yl |
| 385. | 1-CH₃—3-Cl—Pyrazol-5-yl |
| 386. | 1,3-(CH₃)₂—Pyrazol-5-yl |
| 387. | 4-Pyrazolyl |
| 388. | 3-Cl—Pyrazol-4-yl |
| 389. | 3-CH₃—Pyrazol-4-yl |
| 390. | 1-CH₃—Pyrazol-4-yl |
| 391. | 1-CH₃—3-Cl—Pyrazol-4-yl |
| 392. | 1,3-(CH₃)₂—Pyrazol-4-yl |
| 393. | 1,3,4-Oxadiazol-5-yl |
| 394. | 2-CH₃—1,3,4-Oxadiazol-5-yl |
| 395. | 2-Cl—1,3,4-Oxadiazol-5-yl |
| 396. | 2-CF₃—1,3,4-Oxadiazol-5-yl |
| 397. | 2-i-C₃H₇—1,3,4-Oxadiazol-5-yl |
| 398. | 2-CH₃O—1,3,4-Oxadiazol-5-yl |
| 399. | 1,2,4-Oxadiazol-3-yl |
| 400. | 5-CH₃—1,2,4-Oxadiazol-3-yl |
| 401. | 5-i-C₃H₇—1,2,4-Oxadiazol-3-yl |
| 402. | 5-Cl-1,2,4-Oxadiazol-3-yl |
| 403. | 5-CF₃—1,2,4-Oxadiazol-3-yl |
| 404. | 1,2,4-Triazol-3-yl |
| 405. | 1-CH₃—1,2,4-Triazol-3-yl |
| 406. | 1-Pyrrolyl |
| 407. | 3-CH₃—Pyrrol-1-yl |
| 408. | 1-Pyrazolyl |
| 409. | 3-CH₃—Pyrazol-1-yl |
| 410. | 3-CF₃—Pyrazol-1-yl |
| 411. | 4-CH₃—Pyrazol-1-yl |
| 412. | 4-Cl—Pyrazol-1-yl |
| 413. | 4-Ethoxycarbonyl-Pyrazol-1-yl |
| 414. | 3-CH₃—4-Br—Pyrazol-1-yl |
| 415. | 1-Imidazolyl |
| 416. | 4-CH₃—Imidazol-1-yl |
| 417. | 4,5-Cl₂—Imidazol-1-yl |
| 418. | 2,4-(CH₃)₂—Imidazol-1-yl |
| 419. | 1,2,4-Triazol-1-yl |
| 420. | 1,3,4-Triazol-1-yl |
| 421. | 3,5-(CH₃)₂—1,2,4-Triazol-1-yl |
| 422. | 1-Piperidinyl |
| 423. | 1-Pyrrolidinyl |
| 424. | 1-Morphoiinyl |
| 425. | 2-Δ²—Thiazolinyl |
| 426. | 5-CH₃—Δ²—Thiazolin-2-yl |
| 427. | 5,5-(CH₃)₂—Δ²—Thiazolin-2-yl |
| 428. | 4,5-(CH₃)₂—Δ2-Thiazolin-2-yl |
| 429. | 2-Δ²—Oxazolinyl |
| 430. | 4-CH₃—Δ²—Oxazolin-2-yl |
| 431. | 4,4-(CH₃)₂—Δ²—Oxazolin-2-yl |
| 432. | [structure: 6-membered ring with S, N, and methyl substituent] |
| 433. | [structure: 6-membered ring with O, N, and methyl substituent] |
| 434. | [structure: 6-membered ring with O, N, and three CH₃ substituents] |
| 435. | Cyclopropoxy |
| 436. | Cyclobutoxy |
| 437. | Cyclopentoxy |
| 438. | Cyclohexyloxy |
| 439. | Phenoxy |
| 440. | 1-Naphthyloxy |
| 441. | 2-Naphthyloxy |
| 442. | 2-F—C₆H₄O |
| 443. | 3-F—C₆H₄O |
| 444. | 4-F—C₆H₄O |
| 445. | 2,3-F₂—C₆H₃O |
| 446. | 2,4-F₂—C₆H₃O |
| 447. | 2,5-F₂—C₆H₃O |
| 448. | 2,6-F₂—C₆H₃O |
| 449. | 3,4-F₂—C₆H₃O |
| 450. | 3,5-F₂—C₆H₃O |
| 451. | 2-Cl—C₆H₄O |
| 452. | 3-Cl—C₆H₄O |
| 453. | 4-Cl—C₆H₄O |
| 454. | 2,3-Cl₂—C₆H₃O |
| 455. | 2,4-Cl₂—C₆H₃O |
| 456. | 2,5-Cl₂—C₆H₃O |
| 457. | 2,6-Cl₂—C₆H₃O |
| 458. | 3,4-Cl₂—C₆H₃O |
| 459. | 3,5-Cl₂—C₆H₃O |
| 460. | 2,3,4-Cl₃—C₆H₂O |
| 461. | 2,3,5-Cl₃—C₆H₂O |
| 462. | 2,3,6-Cl₃—C₆H₂O |
| 463. | 2,4,5-Cl₃—C₆H₂O |
| 464. | 2,4,6-Cl₃—C₆H₂O |
| 465. | 3,4,5-Cl₃—C₆H₂O |
| 466. | 2-Br—C₆H₄O |
| 467. | 3-Br—C₆H₄O |
| 468. | 4-Br—C₆H₄O |
| 469. | 2,3-Br₂—C₆H₃O |
| 470. | 2,4-Br₂—C₆H₃O |
| 471. | 2,5-Br₂—C₆H₃O |
| 472. | 2,6-Br₂—C₆H₃O |
| 473. | 3,4-Br₂—C₆H₃O |
| 474. | 3,5-Br₂—C₆H₃O |
| 475. | 2-F-3-Cl—C₆H₃O |
| 476. | 2-F-4-Cl—C₆H₃O |
| 477. | 2-F-5-Cl—C₆H₃O |
| 478. | 2-F-3-Br—C₆H₃O |
| 479. | 2-F-4-Br—C₆H₃O |
| 480. | 2-F-5-Br—C₆H₃O |
| 481. | 2-Cl-3-Br—C₆H₃O |
| 482. | 2-Cl-4-Br—C₆H₃O |
| 483. | 2-Cl-5-Br—C₆H₃O |
| 484. | 3-F-4-Cl—C₆H₃O |

TABLE A-continued

| No. | R₃ |
|---|---|
| 485. | 3-F-5-Cl—C₆H₃O |
| 486. | 3-F-6-Cl—C₆H₃O |
| 487. | 3-F-4-Br—C₆H₃O |
| 488. | 3-F-5-Br—C₆H₃O |
| 489. | 3-F-6-Br—C₆H₃O |
| 490. | 3-Cl-4-Br—C₆H₃O |
| 491. | 3-Cl-5-Br—C₆H₃O |
| 492. | 3-Cl-6-Br—C₆H₃O |
| 493. | 4-F-5-Cl—C₆H₃O |
| 494. | 4-F-6-Cl—C₆H₃O |
| 495. | 4-F-5-Br—C₆H₃O |
| 496. | 4-F-6-Br—C₆H₃O |
| 497. | 4-Cl-5-Br—C₆H₃O |
| 498. | 5-F-6-Cl—C₆H₃O |
| 499. | 5-F-6-Br—C₆H₃O |
| 500. | 5-Cl-6-Br—C₆H₃O |
| 501. | 3-Br-4-Cl-5-Br—C₆H₂O |
| 502. | 2-CN—C₆H₄O |
| 503. | 3-CN—C₆H₄O |
| 504. | 4-CN—C₆H₄O |
| 505. | 4-Dimethylaminocarbonyl—C₆H₄O |
| 506. | 2-(N—Methylaminocarbonyl)—C₆H₄O |
| 507. | 3-(N—Methylaminocarbonyl)—C₆H₄O |
| 508. | 4-(N—Methylaminocarbonyl)—C₆H₄O |
| 509. | 2-CH₃S—C₆H₄O |
| 510. | 3-CH₃S—C₆H₄O |
| 511. | 4-CH₃S—C₆H₄O |
| 512. | 2-CH₃SO₂—C₆H₄O |
| 513. | 3-CH₃SO₂—C₆H₄O |
| 514. | 4-CH₃SO₂—C₆H₄O |
| 515. | 2-CF₃O—C₆H₄O |
| 516. | 3-CF₃O—C₆H₄O |
| 517. | 4-CF₃O—C₆H₄O |
| 518. | 2-CHF₂O—C₆H₄O |
| 519. | 4-CHF₂O—C₆H₄O |
| 520. | 4-CHF₂O—C₆H₄O |
| 521. | 3-CF₃, 4-CF₃O—C₆H₃O |
| 522. | 2-CH₃NH—C₆H₄O |
| 523. | 3-CH₃NH—C₆H₄O |
| 524. | 4-CH₃NH—C₆H₄O |
| 525. | 2-(CH₃)₂N—C₆H₄O |
| 526. | 3-(CH₃)₂N—C₆H₄O |
| 527. | 4-(CH₃)₂N—C₆H₄O |
| 528. | 2-Ethoxycarbonyl—C₆H₄O |
| 529. | 3-Ethoxycarbonyl—C₆H₄O |
| 530. | 4-Ethoxycarbonyl—C₆H₄O |
| 531. | 2-CH₂FCH₂—C₆H₄O |
| 532. | 3-CH₂FCH₂—C₆H₄O |
| 533. | 4-CH₂FCH₂—C₆H₄O |
| 534. | 2-CF₃CH₂—C₆H₄O |
| 535. | 3-CF₃CH₂—C₆H₄O |
| 536. | 4-CF₃CH₂—C₆H₄O |
| 537. | 2-CHF₂CF₂—C₆H₄O |
| 538. | 3-CHF₂CF₂—C₆H₄O |
| 539. | 4-CHF₂CF₂—C₆H₄O |
| 540. | 2-CHF₂—C₆H₄O |
| 541. | 3-CHF₂—C₆H₄O |
| 542. | 4-CHF₂—C₆H₄O |
| 543. | 2-CH₃O—C₆H₄O |
| 544. | 3-CH₃O—C₆H₄O |
| 545. | 4-CH₃O—C₆H₄O |
| 546. | 2,3-(CH₃O)₂—C₆H₃O |
| 547. | 2,4-(CH₃O)₂—C₆H₃O |
| 548. | 2,5-(CH₃O)₂—C₆H₃O |
| 549. | 3,4-(CH₃O)₂—C₆H₃O |
| 550. | 3,5-(CH₃O)₂—C₆H₃O |
| 551. | 3,4,5-(CH₃O)₃—C₆H₂O |
| 552. | 2-C₂H₅O—C₆H₄O |
| 553. | 3-C₂H₅O—C₆H₄O |
| 554. | 4-C₂H₅O—C₆H₄O |
| 555. | 2-(n-C₃H₇O)—C₆H₄O |
| 556. | 3-(n-C₃H₇O)—C₆H₄O |
| 557. | 4-(n-C₃H₇O)—C₆H₄O |
| 558. | 2-(i-C₃H₇O)—C₆H₄O |
| 559. | 3-(i-C₃H₇O)—C₆H₄O |
| 560. | 4-(i-C₃H₇O)—C₆H₄O |
| 561. | 4-(n-C₄H₉O)—C₆H₄O |
| 562. | 3-(t-C₄H₉O)—C₆H₄O |
| 563. | 4-(t-C₄H₉O)—C₆H₄O |
| 564. | 2-Allyl—O—C₆H₄O |
| 565. | 3-Allyl—O—C₆H₄O |
| 566. | 4-Allyl—O—C₆H₄O |
| 567. | 2-CF₃—C₆H₄O |
| 568. | 3-CF₃—C₆H₄O |
| 569. | 4-CF₃—C₆H₄O |
| 570. | 2-Acetyl—C₆H₄O |
| 571. | 3-Acetyl—C₆H₄O |
| 572. | 4-Acetyl—C₆H₄O |
| 573. | 2-Methoxycarbonyl—C₆H₄O |
| 574. | 3-Methoxycarbonyl—C₆H₄O |
| 575. | 4-Methoxycarbonyl—C₆H₄O |
| 576. | 2-Aminocarbonyl—C₆H₄O |
| 577. | 3-Aminocarbonyl—C₆H₄O |
| 578. | 4-Aminocarbonyl—C₆H₄O |
| 579. | 2-Dimethylaminocarbonyl—C₆H₄O |
| 580. | 3-Dimethylaminocarbonyl—C₆H₄O |
| 581. | 2-NO₂—C₆H₄O |
| 582. | 3-NO₂—C₆H₄O |
| 583. | 4-NO₂—C₆H₄O |
| 584. | 2-CH₃—C₆H₄O |
| 585. | 3-CH₃—C₆H₄O |
| 586. | 4-CH₃—C₆H₄O |
| 587. | 2,3-(CH₃)₂—C₆H₃O |
| 588. | 2,4-(CH₃)₂—C₆H₃O |
| 589. | 2,5-(CH₃)₂—C₆H₃O |
| 590. | 2,6-(CH₃)₂—C₆H₃O |
| 591. | 3,4-(CH₃)₂—C₆H₃O |
| 592. | 3,5-(CH₃)₂—C₆H₃O |
| 593. | 2-C₂H₅—C₆H₄O |
| 594. | 3-C₂H₅—C₆H₄O |
| 595. | 4-C₂H₅—C₆H₄O |
| 596. | 2-i-C₃H₇—C₆H₄O |
| 597. | 3-i-C₃H₇—C₆H₄O |
| 598. | 4-i-C₃H₇—C₆H₄O |
| 599. | 3-tert.-C₄H₉—C₆H₄O |
| 600. | 4-tert.-C₄H₉—C₆H₄O |
| 601. | 2-Vinyl—C₆H₄O |
| 602. | 3-Vinyl—C₆H₄O |
| 603. | 4-Vinyl—C₆H₄O |
| 604. | 2-Allyl—C₆H₄O |
| 605. | 3-Allyl—C₆H₄O |
| 606. | 4-Allyl-C₆H₄O |
| 607. | 2-C₆H₅—C₆H₄O |
| 608. | 3-C₆H₅—C₆H₄O |
| 609. | 4-C₆H₅—C₆H₄O |
| 610. | 3-CH₃-5-t-C₄H₉—C₆H₃O |
| 611. | 2-F-4-CH₃—C₆H₃O |
| 612. | 2-F-5-CH₃—C₆H₃O |
| 613. | 2-CH₃-4-F—C₆H₃O |
| 614. | 2-CH₃-5-F—C₆H₃O |
| 615. | 2-CH₃-4-Cl—C₆H₃O |
| 616. | 2-Pyridyloxy |
| 617. | 3-Pyridyloxy |
| 618. | 4-Pyridyloxy |
| 619. | 2-Pyrimidinyloxy |
| 620. | 4-Pyrimidinyloxy |
| 621. | 5-Pyrimidinyloxy |
| 622. | 1-CH₃—Piperidinyl-3-oxy |
| 623. | 1-CH₃—Piperidinyl-4-oxy |

Details relating to physical data in the Tables which follow

°=m.p. in ° Celsius

Number=chemical shift of $R_4$ in $^1$H-NMR ($\delta$ in ppm);

*cis-trans isomers

TABLE 67

Compounds of formula

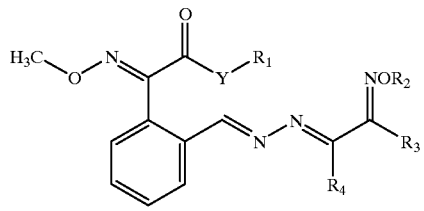

| No. | Y | $R_1$ | $R_2$ | $R_3$ | $R_4$ | Phys. data |
|---|---|---|---|---|---|---|
| 67.1. | O | $CH_3$ | $CH_3$ | $CH_3$ | $CH_3$ | 118–119° |
| 67.2. | O | $CH_3$ | $CH_2CH_3$ | $CH_3$ | $CH_3$ | 78–81° |
| 67.3. | O | $CH_3$ | $(CH_2)_2CH_3$ | $CH_3$ | $CH_3$ | 2.08/2.20 ($R_3$ & $R_4$) |
| 67.4. | O | $CH_3$ | $CH_2F$ | $CH_3$ | $CH_3$ | 120–122° |
| 67.5. | O | $CH_3$ | $CH_2CF_3$ | $CH_3$ | $CH_3$ | 98–99° |
| 67.6. | O | $CH_3$ | $CH_3$ | 4-$CH_3$—$C_6H_4$ | $CH_3$ | 113–115° |
| 67.7. | O | $CH_3$ | $CH_3$ | 4-$CH_3CH_2$—$C_6H_4$ | $CH_3$ | 117–118° |
| 67.8. | O | $CH_3$ | $CH_3$ | 4-F—$C_6H_4$ | $CH_3$ | 101–103° |
| 67.9. | O | $CH_3$ | $CH_3$ | 4-Cl—$C_6H_4$ | $CH_3$ | 104–105° |
| 67.10. | O | $CH_3$ | $CH_3$ | 4-Br—$C_6H_4$ | $CH_3$ | 124–127° |
| 67.11. | O | $CH_3$ | $CH_3$ | 4-$CH_3O$—$C_6H_4$ | $CH_3$ | 118–120° |
| 67.12. | O | $CH_3$ | $CH_3$ | 3-$CF_3$—$C_6H_4$ | $CH_3$ | 112–113° |
| 67.13. | O | $CH_3$ | $CH_3$ | 4-$CH_3CH_2O$—$C_6H_4$ | $CH_3$ | 109–111° |

TABLE 68

Compounds of formula

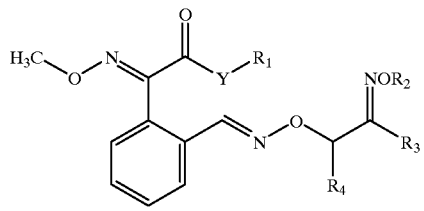

| No. | Y | $R_1$ | $R_2$ | $R_3$ | $R_4$ | Phys. data |
|---|---|---|---|---|---|---|
| 68.1. | O | $CH_3$ | $CH_3$ | $CH_3$ | $CH_3$ | 1.40 |
| 68.2. | O | $CH_3$ | $CH_3$ | 4-Cl—$C_6H_4$ | $CH_3$ | 1.41/1.57* |
| 68.3. | O | $CH_3$ | $CH_3$ | 2,4-$(Cl)_2$—$C_6H_3$ | $CH_3$ | 1.46/1.54* |
| 68.4. | O | $CH_2CH_3$ | $CH_3$ | 2,4-$(Cl)_2$—$C_6H_3$ | $CH_3$ | 1.56 |
| 68.5. | O | $CH_3$ | $CH_3$ | 4-$CH_3O$—$C_6H_4$ | $CH_3$ | 1.43/1.57* |
| 68.6. | O | $CH_3$ | $CH_2CH_3$ | 2,4-$(F)_2$—$C_6H_3$ | $CH_3$ | 1.43/1.58* |
| 68.7. | O | $CH_3$ | $CH_3$ | 2-F-4-$CH_3O$—$C_6H_3$ | $CH_3$ | 1.42/1.57* |
| 68.8. | O | $CH_3$ | $CH_3$ | 2-F-4-$CH_3CH_2O$—$C_6H_3$ | $CH_3$ | 1.42/1.57* |
| 68.9. | O | $CH_3$ | $CH_3$ | 2-F-4-i-$C_3H_7O$—$C_6H_3$ | $CH_3$ | 1.42/1.57* |
| 68.10. | O | $CH_3$ | $CH_3$ | 2,5-$(CH_3)_2$—$C_6H_3$ | $CH_3$ | 1.43/1.54* |
| 68.11. | O | $CH_3$ | $CH_2CH_3$ | 4-(4-chlorophenoxy)—$C_6H_4$ | $CH_3$ | 1.44/1.59* |
| 68.12. | NH | $CH_3$ | $CH_3$ | $CH_3$ | $CH_3$ | 1.37 |
| 68.13. | NH | $CH_3$ | $CH_3$ | 4-Cl—$C_6H_4$ | $CH_3$ | 1.35/1.53* |
| 68.14. | NH | $CH_3$ | $CH_3$ | 2,4-$(Cl)_2$—$C_6H_3$ | $CH_3$ | 1.51 |
| 68.15. | NH | $CH_3$ | $CH_3$ | 4-$CH_3O$—$C_6H_4$ | $CH_3$ | 1.36/1.53* |
| 68.16. | NH | $CH_3$ | $CH_2CH_3$ | 2,4-$(F)_2$—$C_6H_3$ | $CH_3$ | 1.38/1.56* |
| 68.17. | NH | $CH_3$ | $CH_3$ | 2-F-4-$CH_3O$—$C_6H_3$ | $CH_3$ | 1.35/1.54* |
| 68.18. | NH | $CH_3$ | $CH_3$ | 2-F-4-$CH_3CH_2O$—$C_6H_3$ | $CH_3$ | 1.41/1.54* |
| 68.19. | NH | $CH_3$ | $CH_3$ | 2-F-4-i-$C_3H_7$—$C_6H_3$ | $CH_3$ | 1.35/1.54* |
| 68.20. | NH | $CH_3$ | $CH_3$ | 2,5-$(CH_3)_2$—$C_6H_5$ | $CH_3$ | 1.31/1.51* |
| 68.21. | NH | $CH_3$ | $CH_2CH_3$ | 4-(4-chlorophenoxy)—$C_6H_4$ | $CH_3$ | 1.37/1.56* |

TABLE 69

Intermediate products of formula II

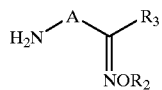

II

| No. | A | $R_2$ | $R_3$ | $R_4$ | Phys. data |
|---|---|---|---|---|---|
| 69.1. | $N=CR_4$ | $CH_3$ | $4\text{-}CH_3\text{--}C_6H_4$ | $CH_3$ | 112–114° |
| 69.2. | $N=CR_4$ | $CH_3$ | $4\text{-}CH_3CH_2\text{--}C_6H_4$ | $CH_3$ | 92–95° |
| 69.3. | $N=CR_4$ | $CH_3$ | $4\text{-}F\text{--}C_6H_4$ | $CH_3$ | 134–136° |
| 69.4. | $N=CR_4$ | $CH_3$ | $4\text{-}Cl\text{--}C_6H_4$ | $CH_3$ | 118–119° |
| 69.5. | $N=CR_4$ | $CH_3$ | $4\text{-}Br\text{--}C_6H_4$ | $CH_3$ | 127–129° |
| 69.6. | $N=CR_4$ | $CH_3$ | $4\text{-}CH_3O\text{--}C_6H_4$ | $CH_3$ | 87–90° |
| 69.7. | $N=CR_4$ | $CH_3$ | $4\text{-}CH_3CH_2O\text{--}C_6H_4$ | $CH_3$ | 92–94° |
| 69.8. | $N=CR_4$ | $CH_3$ | $3\text{-}CF_3\text{--}C_6H_4$ | $CH_3$ | 96–98° |
| 69.9. | $N=CR_4$ | $CH_3$ | $CH_3$ | $CH_3$ | 94–97° |
| 69.10. | $N=CR_4$ | $CH_3$ | $OCH(CH_3)_2$ | $CH_3$ | |

TABLE 70

Intermediate products of formula X

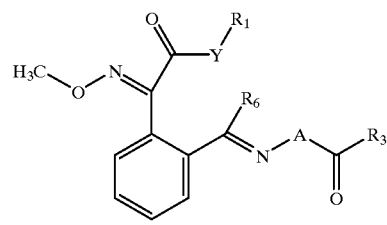

X

| No. | Y | A | $R_1$ | $R_3$ | $R_4$ | $R_6$ | Phys. data |
|---|---|---|---|---|---|---|---|
| 70.1. | O | $OCHR_4$ | $CH_3$ | $CH_3$ | $CH_3$ | H | 1.39 |
| 70.2. | O | $OCHR_4$ | $CH_3$ | $4\text{-}Cl\text{--}C_6H_4$ | $CH_3$ | H | 1.55 |
| 70.3. | O | $OCHR_4$ | $CH_3$ | $4\text{-}CH_3O\text{--}C_6H_4$ | $CH_3$ | H | 1.55 |
| 70.4. | O | $OCHR_4$ | $CH_3$ | $2,4\text{-}(F)_2\text{--}C_6H_3$ | $CH_3$ | H | 1.53 |
| 70.5. | O | $OCHR_4$ | $CH_2CH_3$ | $2,4\text{-}(Cl)_2\text{--}C_6H_3$ | $CH_3$ | H | 1.53 |
| 70.6. | O | $OCHR_4$ | $CH_3$ | $2\text{-}F\text{-}4\text{-}CH_3O\text{--}C_6H_3$ | $CH_3$ | H | 1.53 |
| 70.7. | O | $OCHR_4$ | $CH_3$ | $2\text{-}F\text{-}4\text{-}CH_3CH_2O\text{--}C_6H_3$ | $CH_3$ | H | 1.54 |
| 70.8. | O | $OCHR_4$ | $CH_3$ | $2\text{-}F\text{-}4\text{-}i\text{-}C_3H_7O\text{--}C_6H_3$ | $CH_3$ | H | 1.53 |
| 70.9. | O | $OCHR_4$ | $CH_3$ | $2,5\text{-}(CH_3)_2\text{--}C_6H_3$ | $CH_3$ | H | 1.47 |
| 70.10. | O | $OCHR_4$ | $CH_3$ | $4\text{-}(4\text{-chlorophenoxy})\text{--}C_6H_4$ | $CH_3$ | H | 1.57 |
| 70.11. | NH | $OCHR_4$ | $CH_3$ | $4\text{-}CH_3O\text{--}C_6H_4$ | $CH_3$ | H | 1.56 |

TABLE 71

Intermediate products of formula IX

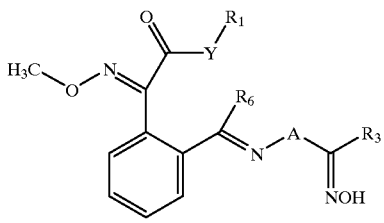

IX

| No. | Y | A | $R_1$ | $R_3$ | $R_4$ | $R_6$ | Phys. data |
|---|---|---|---|---|---|---|---|
| 71.1. | O | N=CR$_4$ | CH$_3$ | CH$_3$ | CH$_3$ | H | 148–149° |
| 71.2. | O | OCHR$_4$ | CH$_3$ | CH$_3$ | CH$_3$ | H | 1.41 |
| 71.3. | O | N=CR$_4$ | CH$_3$ | 4-CH$_3$—C$_6$H$_4$ | CH$_3$ | H | |
| 71.4. | O | N=CR$_4$ | CH$_3$ | 4-CH$_3$CH$_2$—C$_6$H$_4$ | CH$_3$ | H | |
| 71.5. | O | N=CR$_4$ | CH$_3$ | 4-F—C$_6$H$_4$ | CH$_3$ | H | |
| 71.6. | O | N=CR$_4$ | CH$_3$ | 4-Cl—C$_6$H$_4$ | CH$_3$ | H | |
| 71.7. | O | N=CR$_4$ | CH$_3$ | 4-Br—C$_6$H$_4$ | CH$_3$ | H | |
| 71.8. | O | N=CR$_4$ | CH$_3$ | 4-CH$_3$O—C$_6$H$_4$ | CH$_3$ | H | |
| 71.9. | O | N=CR$_4$ | CH$_3$ | 4-CH$_3$CH$_2$O—C$_6$H$_4$ | CH$_3$ | H | |
| 71.10 | O | N=CR$_4$ | CH$_3$ | 3-CF$_3$—C$_6$H$_4$ | CH$_3$ | H | |
| 71.11. | O | N=CR$_4$ | CH$_3$ | OCH$_3$ | CH$_3$ | H | |
| 71.12. | O | N=CR$_4$ | CH$_3$ | OCH(CH$_3$)$_2$ | CH$_3$ | H | |
| 71.13. | O | N=CR$_4$ | CH$_3$ | 4-CH$_3$—C$_6$H$_4$ | CH$_3$ | CH$_3$ | |
| 71.14. | O | N=CR$_4$ | CH$_3$ | 4-CH$_3$CH$_2$—C$_6$H$_4$ | CH$_3$ | CH$_3$ | |
| 71.15. | O | N=CR$_4$ | CH$_3$ | 4-F—C$_6$H$_4$ | CH$_3$ | CH$_3$ | |
| 71.16. | O | N=CR$_4$ | CH$_3$ | 4-Cl—C$_6$H$_4$ | CH$_3$ | CH$_3$ | |
| 71.17. | O | N=CR$_4$ | CH$_3$ | 4-Br—C$_6$H$_4$ | CH$_3$ | CH$_3$ | |
| 71.18. | O | N=CR$_4$ | CH$_3$ | 4-CH$_3$O—C$_6$H$_4$ | CH$_3$ | CH$_3$ | |
| 71.19. | O | N=CR$_4$ | CH$_3$ | 4-CH$_3$CH$_2$O—C$_6$H$_4$ | CH$_3$ | CH$_3$ | |
| 71.20. | O | N=CR$_4$ | CH$_3$ | 3-CF$_3$—C$_6$H$_4$ | CH$_3$ | CH$_3$ | |
| 71.21. | O | N=CR$_4$ | CH$_3$ | CH$_3$ | CH$_3$ | CH$_3$ | |
| 71.22. | O | N=CR$_4$ | CH$_3$ | OCH(CH$_3$)$_2$ | CH$_3$ | CH$_3$ | |

TABLE 72

Intermediate products of formula XV

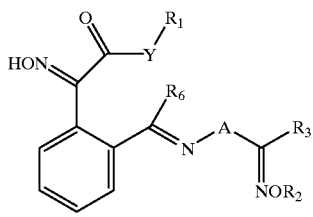

XV

| No | Y | A | $R_1$ | $R_2$ | $R_3$ | $R_4$ | $R_6$ |
|---|---|---|---|---|---|---|---|
| 72.1. | O | N=CR$_4$ | CH$_3$ | CH$_3$ | 4-CH$_3$—C$_6$H$_4$ | CH$_3$ | H |
| 72.2. | O | N=CR$_4$ | CH$_3$ | CH$_3$ | 4-CH$_3$CH$_2$—C$_6$H$_4$ | CH$_3$ | H |
| 72.3. | O | N=CR$_4$ | CH$_3$ | CH$_3$ | 4-F—C$_6$H$_4$ | CH$_3$ | H |
| 72.4. | O | N=CR$_4$ | CH$_3$ | CH$_3$ | 4-Cl—C$_6$H$_4$ | CH$_3$ | H |
| 72.5. | O | N=CR$_4$ | CH$_3$ | CH$_3$ | 4-Br—C$_6$H$_4$ | CH$_3$ | H |
| 72.6. | O | N=CR$_4$ | CH$_3$ | CH$_3$ | 4-CH$_3$O—C$_6$H$_4$ | CH$_3$ | H |
| 72.7. | O | N=CR$_4$ | CH$_3$ | CH$_3$ | 4-CH$_3$CH$_2$O—C$_6$H$_4$ | CH$_3$ | H |
| 72.8. | O | N=CR$_4$ | CH$_3$ | CH$_3$ | 3-CF$_3$—C$_6$H$_4$ | CH$_3$ | H |
| 72.9. | O | N=CR$_4$ | CH$_3$ | CH$_3$ | CH$_3$ | CH$_3$ | H |
| 72.10. | O | N=CR$_4$ | CH$_3$ | CH$_3$ | OCH(CH$_3$)$_2$ | CH$_3$ | H |
| 72.11. | O | N=CR$_4$ | CH$_3$ | CH$_3$ | 4-CH$_3$—C$_6$H$_4$ | CH$_3$ | CH$_3$ |
| 72.12. | O | N=CR$_4$ | CH$_3$ | CH$_3$ | 4-CH$_3$CH$_2$—C$_6$H$_4$ | CH$_3$ | CH$_3$ |
| 72.13. | O | N=CR$_4$ | CH$_3$ | CH$_3$ | 4-F—C$_6$H$_4$ | CH$_3$ | CH$_3$ |
| 72.14. | O | N=CR$_4$ | CH$_3$ | CH$_3$ | 4-Cl—C$_6$H$_4$ | CH$_3$ | CH$_3$ |
| 72.15. | O | N=CR$_4$ | CH$_3$ | CH$_3$ | 4-Br—C$_6$H$_4$ | CH$_3$ | CH$_3$ |

TABLE 72-continued

Intermediate products of formula XV

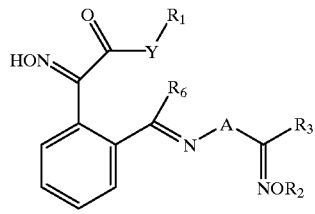

XV

| No | Y | A | $R_1$ | $R_2$ | $R_3$ | $R_4$ | $R_6$ |
|---|---|---|---|---|---|---|---|
| 72.16. | O | $N=CR_4$ | $CH_3$ | $CH_3$ | 4-$CH_3O$—$C_6H_4$ | $CH_3$ | $CH_3$ |
| 72.17. | O | $N=CR_4$ | $CH_3$ | $CH_3$ | 4-$CH_3CH_2O$—$C_6H_4$ | $CH_3$ | $CH_3$ |
| 72.18. | O | $N=CR_4$ | $CH_3$ | $CH_3$ | 3-$CF_3$—$C_6H_4$ | $CH_3$ | $CH_3$ |
| 72.19. | O | $N=CR_4$ | $CH_3$ | $CH_3$ | $CH_3$ | $CH_3$ | $CH_3$ |
| 72.20. | O | $N=CR_4$ | $CH_3$ | $CH_3$ | $OCH(CH_3)_2$ | $CH_3$ | $CH_3$ |
| 72.21. | NH | $N=CR_4$ | $CH_3$ | $CH_3$ | 4-$CH_3$—$C_6H_4$ | $CH_3$ | H |
| 72.22. | NH | $N=CR_4$ | $CH_3$ | $CH_3$ | 4-$CH_3CH_2$—$C_6H_4$ | $CH_3$ | H |
| 72.23. | NH | $N=CR_4$ | $CH_3$ | $CH_3$ | 4-F—$C_6H_4$ | $CH_3$ | H |
| 72.24. | NH | $N=CR_4$ | $CH_3$ | $CH_3$ | 4-Cl—$C_6H_4$ | $CH_3$ | H |
| 72.25. | NH | $N=CR_4$ | $CH_3$ | $CH_3$ | 4-Br—$C_6H_4$ | $CH_3$ | H |
| 72.26. | NH | $N=CR_4$ | $CH_3$ | $CH_3$ | 4-$CH_3O$—$C_6H_4$ | $CH_3$ | H |
| 72.27. | NH | $N=CR_4$ | $CH_3$ | $CH_3$ | 4-$CH_3CH_2O$—$C_6H_4$ | $CH_3$ | H |
| 72.28. | NH | $N=CR_4$ | $CH_3$ | $CH_3$ | 3-$CF_3$—$C_6H_4$ | $CH_3$ | H |
| 72.29. | NH | $N=CR_4$ | $CH_3$ | $CH_3$ | $CH_3$ | $CH_3$ | H |
| 72.30. | NH | $N=CR_4$ | $CH_3$ | $CH_3$ | $OCH(CH_3)_2$ | $CH_3$ | H |
| 72.31. | NH | $N=CR_4$ | $CH_3$ | $CH_3$ | 4-$CH_3$—$C_6H_4$ | $CH_3$ | $CH_3$ |
| 72.32. | NH | $N=CR_4$ | $CH_3$ | $CH_3$ | 4-$CH_3CH_2$—$C_6H_4$ | $CH_3$ | $CH_3$ |
| 72.33. | NH | $N=CR_4$ | $CH_3$ | $CH_3$ | 4-F—$C_6H_4$ | $CH_3$ | $CH_3$ |
| 72.34. | NH | $N=CR_4$ | $CH_3$ | $CH_3$ | 4-Cl—$C_6H_4$ | $CH_3$ | $CH_3$ |
| 72.35. | NH | $N=CR_4$ | $CH_3$ | $CH_3$ | 4-Br—$C_6H_4$ | $CH_3$ | $CH_3$ |
| 72.36. | NH | $N=CR_4$ | $CH_3$ | $CH_3$ | 4-$CH_3O$—$C_6H_4$ | $CH_3$ | $CH_3$ |
| 72.37. | NH | $N=CR_4$ | $CH_3$ | $CH_3$ | 4-$CH_3CH_2O$—$C_6H_4$ | $CH_3$ | $CH_3$ |
| 72.38. | NH | $N=CR_4$ | $CH_3$ | $CH_3$ | 3-$CF_3$—$C_6H_4$ | $CH_3$ | $CH_3$ |
| 72.39. | NH | $N=CR_4$ | $CH_3$ | $CH_3$ | $CH_3$ | $CH_3$ | $CH_3$ |
| 72.40. | NH | $N=CR_4$ | $CH_3$ | $CH_3$ | $OCH(CH_3)_2$ | $CH_3$ | $CH_3$ |

TABLE 73

Intermediate product of formula XVI

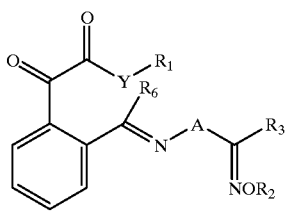

XVI

| No | Y | A | $R_1$ | $R_2$ | $R_3$ | $R_4$ | $R_6$ |
|---|---|---|---|---|---|---|---|
| 73.1. | O | $N=CR_4$ | $CH_3$ | $CH_3$ | 4-$CH_3$—$C_6H_4$ | $CH_3$ | H |
| 73.2. | O | $N=CR_4$ | $CH_3$ | $CH_3$ | 4-$CH_3CH_2$—$C_6H_4$ | $CH_3$ | H |
| 73.3. | O | $N=CR_4$ | $CH_3$ | $CH_3$ | 4-F—$C_6H_4$ | $CH_3$ | H |
| 73.4. | O | $N=CR_4$ | $CH_3$ | $CH_3$ | 4-Cl—$C_6H_4$ | $CH_3$ | H |
| 73.5. | O | $N=CR_4$ | $CH_3$ | $CH_3$ | 4-Br—$C_6H_4$ | $CH_3$ | H |
| 73.6. | O | $N=CR_4$ | $CH_3$ | $CH_3$ | 4-$CH_3O$—$C_6H_4$ | $CH_3$ | H |
| 73.7. | O | $N=CR_4$ | $CH_3$ | $CH_3$ | 4-$CH_3CH_2O$—$C_6H_4$ | $CH_3$ | H |
| 73.8. | O | $N=CR_4$ | $CH_3$ | $CH_3$ | 3-$CF_3$—$C_6H_4$ | $CH_3$ | H |
| 73.9. | O | $N=CR_4$ | $CH_3$ | $CH_3$ | $CH_3$ | $CH_3$ | H |
| 73.10. | O | $N=CR_4$ | $CH_3$ | $CH_3$ | $OCH(CH_3)_2$ | $CH_3$ | H |
| 73.11. | O | $N=CR_4$ | $CH_3$ | $CH_3$ | 4-$CH_3$—$C_6H_4$ | $CH_3$ | $CH_3$ |
| 73.12. | O | $N=CR_4$ | $CH_3$ | $CH_3$ | 4-$CH_3CH_2$—$C_6H_4$ | $CH_3$ | $CH_3$ |
| 73.13. | O | $N=CR_4$ | $CH_3$ | $CH_3$ | 4-F—$C_6H_4$ | $CH_3$ | $CH_3$ |
| 73.14. | O | $N=CR_4$ | $CH_3$ | $CH_3$ | 4-Cl—$C_8H4$ | $CH_3$ | $CH_3$ |
| 73.15. | O | $N=CR_4$ | $CH_3$ | $CH_3$ | 4-Br—$C_6H_4$ | $CH_3$ | $CH_3$ |
| 73.16. | O | $N=CR_4$ | $CH_3$ | $CH_3$ | 4-$CH_3O$—$C_6H_4$ | $CH_3$ | $CH_3$ |
| 73.17. | O | $N=CR_4$ | $CH_3$ | $CH_3$ | 4-$CH_3CH_2O$—$C_6H_4$ | $CH_3$ | $CH_3$ |

TABLE 73-continued

Intermediate product of formula XVI

XVI

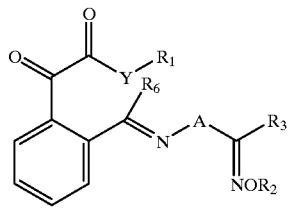

| No | Y | A | $R_1$ | $R_2$ | $R_3$ | $R_4$ | $R_6$ |
|---|---|---|---|---|---|---|---|
| 73.18. | O | $N=CR_4$ | $CH_3$ | $CH_3$ | $3\text{-}CF_3\text{—}C_6H_4$ | $CH_3$ | $CH_3$ |
| 73.19. | O | $N=CR_4$ | $CH_3$ | $CH_3$ | $CH_3$ | $CH_3$ | $CH_3$ |
| 73.20. | O | $N=CR_4$ | $CH_3$ | $CH_3$ | $OCH(CH_3)_2$ | $CH_3$ | $CH_3$ |
| 73.21. | NH | $N=CR_4$ | $CH_3$ | $CH_3$ | $4\text{-}CH_3\text{—}C_6H_4$ | $CH_3$ | H |
| 73.22. | NH | $N=CR_4$ | $CH_3$ | $CH_3$ | $4\text{-}CH_3CH_2\text{—}C_6H_4$ | $CH_3$ | H |
| 73.23. | NH | $N=CR_4$ | $CH_3$ | $CH_3$ | $4\text{-}F\text{—}C_6H_4$ | $CH_3$ | H |
| 73.24. | NH | $N=CR_4$ | $CH_3$ | $CH_3$ | $4\text{-}Cl\text{—}C_6H_4$ | $CH_3$ | H |
| 73.25. | NH | $N=CR_4$ | $CH_3$ | $CH_3$ | $4\text{-}Br\text{—}C_6H_4$ | $CH_3$ | H |
| 73.26. | NH | $N=CR_4$ | $CH_3$ | $CH_3$ | $4\text{-}CH_3O\text{—}C_6H_4$ | $CH_3$ | H |
| 73.27. | NH | $N=CR_4$ | $CH_3$ | $CH_3$ | $4\text{-}CH_3CH_2O\text{—}C_6H_4$ | $CH_3$ | H |
| 73.28. | NH | $N=CR_4$ | $CH_3$ | $CH_3$ | $3\text{-}CF_3\text{—}C_6H_4$ | $CH_3$ | H |
| 73.29. | NH | $N=CR_4$ | $CH_3$ | $CH_3$ | $CH_3$ | $CH_3$ | H |
| 73.30. | NH | $N=CR_4$ | $CH_3$ | $CH_3$ | $OCH(CH_3)_2$ | $CH_3$ | H |
| 73.31. | NH | $N=CR_4$ | $CH_3$ | $CH_3$ | $4\text{-}CH_3\text{—}C_6H_4$ | $CH_3$ | $CH_3$ |
| 73.32. | NH | $N=CR_4$ | $CH_3$ | $CH_3$ | $4\text{-}CH_3CH_2\text{—}C_6H_4$ | $CH_3$ | $CH_3$ |
| 73.33. | NH | $N=CR_4$ | $CH_3$ | $CH_3$ | $4\text{-}F\text{—}C_6H_4$ | $CH_3$ | $CH_3$ |
| 73.34. | NH | $N=CR_4$ | $CH_3$ | $CH_3$ | $4\text{-}Cl\text{—}C_6H_4$ | $CH_3$ | $CH_3$ |
| 73.35. | NH | $N=CR_4$ | $CH_3$ | $CH_3$ | $4\text{-}Br\text{—}C_6H_4$ | $CH_3$ | $CH_3$ |
| 73.36. | NH | $N=CR_4$ | $CH_3$ | $CH_3$ | $4\text{-}CH_3O\text{—}C_6H_4$ | $CH_3$ | $CH_3$ |
| 73.37. | NH | $N=CR_4$ | $CH_3$ | $CH_3$ | $4\text{-}CH_3CH_2O\text{—}C_6H_4$ | $CH_3$ | $CH_3$ |
| 73.38. | NH | $N=CR_4$ | $CH_3$ | $CH_3$ | $3\text{-}CF_3\text{—}C_6H_4$ | $CH_3$ | $CH_3$ |
| 73.39. | NH | $N=CR_4$ | $CH_3$ | $CH_3$ | $CH_3$ | $CH_3$ | $CH_3$ |
| 73.40. | NH | $N=CR_4$ | $CH_3$ | $CH_3$ | $OCH(CH_3)_2$ | $CH_3$ | $CH_3$ |

TABLE 74

Intermediate product of formula XVII

XVII

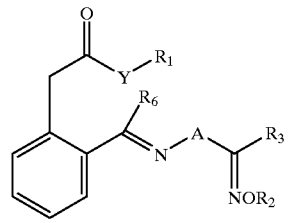

| No | Y | A | $R_1$ | $R_2$ | $R_3$ | $R_4$ | $R_6$ |
|---|---|---|---|---|---|---|---|
| 74.1. | O | $N=CR_4$ | $CH_3$ | $CH_3$ | $4\text{-}CH_3\text{—}C_6H_4$ | $CH_3$ | H |
| 74.2. | O | $N=CR_4$ | $CH_3$ | $CH_3$ | $4\text{-}CH_3CH_2\text{—}C_6H_4$ | $CH_3$ | H |
| 74.3. | O | $N=CR_4$ | $CH_3$ | $CH_3$ | $4\text{-}F\text{—}C_6H_4$ | $CH_3$ | H |
| 74.4. | O | $N=CR_4$ | $CH_3$ | $CH_3$ | $4\text{-}Cl\text{—}C_6H_4$ | $CH_3$ | H |
| 74.5. | O | $N=CR_4$ | $CH_3$ | $CH_3$ | $4\text{-}Br\text{—}C_6H_4$ | $CH_3$ | H |
| 74.6. | O | $N=CR_4$ | $CH_3$ | $CH_3$ | $4\text{-}CH_3O\text{—}C_6H_4$ | $CH_3$ | H |
| 74.7. | O | $N=CR_4$ | $CH_3$ | $CH_3$ | $4\text{-}CH_3CH_2O\text{—}C_6H_4$ | $CH_3$ | H |
| 74.8. | O | $N=CR_4$ | $CH_3$ | $CH_3$ | $3\text{-}CF_3\text{—}C_6H_4$ | $CH_3$ | H |
| 74.9. | O | $N=CR_4$ | $CH_3$ | $CH_3$ | $CH_3$ | $CH_3$ | H |
| 74.10. | O | $N=CR_4$ | $CH_3$ | $CH_3$ | $OCH(CH_3)_2$ | $CH_3$ | H |
| 74.11. | O | $N=CR_4$ | $CH_3$ | $CH_3$ | $4\text{-}CH_3\text{—}C_6H_4$ | $CH_3$ | $CH_3$ |
| 74.12. | O | $N=CR_4$ | $CH_3$ | $CH_3$ | $4\text{-}CH_3CH_2\text{—}C_6H_4$ | $CH_3$ | $CH_3$ |
| 74.13. | O | $N=CR_4$ | $CH_3$ | $CH_3$ | $4\text{-}F\text{—}C_6H_4$ | $CH_3$ | $CH_3$ |
| 74.14. | O | $N=CR_4$ | $CH_3$ | $CH_3$ | $4\text{-}Cl\text{—}C_6H_4$ | $CH_3$ | $CH_3$ |
| 74.15. | O | $N=CR_4$ | $CH_3$ | $CH_3$ | $4\text{-}Br\text{—}C_6H_4$ | $CH_3$ | $CH_3$ |
| 74.16. | O | $N=CR_4$ | $CH_3$ | $CH_3$ | $4\text{-}CH_3O\text{—}C_6H_4$ | $CH_3$ | $CH_3$ |
| 74.17. | O | $N=CR_4$ | $CH_3$ | $CH_3$ | $4\text{-}CH_3CH_2O\text{—}C_6H_4$ | $CH_3$ | $CH_3$ |
| 74.18. | O | $N=CR_4$ | $CH_3$ | $CH_3$ | $3\text{-}CF_3\text{—}C_6H_4$ | $CH_3$ | $CH_3$ |

TABLE 74-continued

Intermediate product of formula XVII

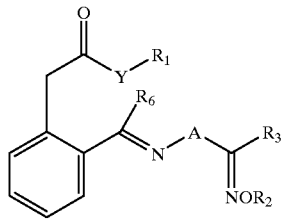

XVII

| No | Y | A | $R_1$ | $R_2$ | $R_3$ | $R_4$ | $R_6$ |
|---|---|---|---|---|---|---|---|
| 74.19. | O | N=CR$_4$ | CH$_3$ | CH$_3$ | CH$_3$ | CH$_3$ | CH$_3$ |
| 74.20. | O | N=CR$_4$ | CH$_3$ | CH$_3$ | OCH(CH$_3$)$_2$ | CH$_3$ | CH$_3$ |

TABLE 75

Intermediate products of formula XVIII

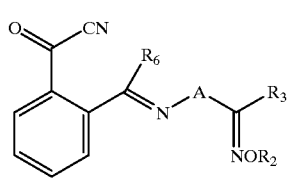

XVIII

| No | A | $R_2$ | $R_3$ | $R_4$ | $R_6$ |
|---|---|---|---|---|---|
| 75.1. | N=CR$_4$ | CH$_3$ | 4-CH$_3$—C$_6$H$_4$ | CH$_3$ | H |
| 75.2. | N=CR$_4$ | CH$_3$ | 4-CH$_3$CH$_2$—C$_6$H$_4$ | CH$_3$ | H |
| 75.3. | N=CR$_4$ | CH$_3$ | 4-F—C$_6$H$_4$ | CH$_3$ | H |
| 75.4. | N=CR$_4$ | CH$_3$ | 4-Cl—C$_6$H$_4$ | CH$_3$ | H |
| 75.5. | N=CR$_4$ | CH$_3$ | 4-Br—C$_6$H$_4$ | CH$_3$ | H |
| 75.6. | N=CR$_4$ | CH$_3$ | 4-CH$_3$O—C$_6$H$_4$ | CH$_3$ | H |
| 75.7. | N=CR$_4$ | CH$_3$ | 4-CH$_3$CH$_2$O—C$_6$H$_4$ | CH$_3$ | H |
| 75.8. | N=CR$_4$ | CH$_3$ | 3-CF$_3$—C$_6$H$_4$ | CH$_3$ | H |
| 75.9. | N=CR$_4$ | CH$_3$ | CH$_3$ | CH$_3$ | H |
| 75.10. | N=CR$_4$ | CH$_3$ | OCH(CH$_3$)$_2$ | CH$_3$ | H |
| 75.11. | N=CR$_4$ | CH$_3$ | 4-CH$_3$—C$_6$H$_4$ | CH$_3$ | CH$_3$ |
| 75.12. | N=CR$_4$ | CH$_3$ | 4-CH$_3$CH$_2$—C$_6$H$_4$ | CH$_3$ | CH$_3$ |
| 75.13. | N=CR$_4$ | CH$_3$ | 4-F—C$_6$H$_4$ | CH$_3$ | CH$_3$ |
| 75.14. | N=CR$_4$ | CH$_3$ | 4-Cl—C$_6$H$_4$ | CH$_3$ | CH$_3$ |
| 75.15. | N=CR$_4$ | CH$_3$ | 4-Br—C$_6$H$_4$ | CH$_3$ | CH$_3$ |
| 75.16. | N=CR$_4$ | CH$_3$ | 4-CH$_3$O—C$_6$H$_4$ | CH$_3$ | CH$_3$ |
| 75.17. | N=CR$_4$ | CH$_3$ | 4-CH$_3$CH$_2$O—C$_6$H$_4$ | CH$_3$ | CH$_3$ |
| 75.18. | N=CR$_4$ | CH$_3$ | 3-CF$_3$—C$_6$H$_4$ | CH$_3$ | CH$_3$ |
| 75.19. | N=CR$_4$ | CH$_3$ | CH$_3$ | CH$_3$ | CH$_3$ |
| 75.20. | N=CR$_4$ | CH$_3$ | OCH(CH$_3$)$_2$ | CH$_3$ | CH$_3$ |

TABLE 76

Intermediate products of formula XXI

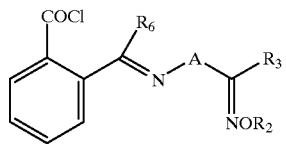

XXI

| No | A | $R_2$ | $R_3$ | $R_4$ | $R_6$ |
|---|---|---|---|---|---|
| 76.1. | N=CR$_4$ | CH$_3$ | 4-CH$_3$—C$_6$H$_4$ | CH$_3$ | H |
| 76.2. | N=CR$_4$ | CH$_3$ | 4-CH$_3$CH$_2$—C$_6$H$_4$ | CH$_3$ | H |
| 76.3. | N=CR$_4$ | CH$_3$ | 4-F—C$_6$H$_4$ | CH$_3$ | H |
| 76.4. | N=CR$_4$ | CH$_3$ | 4-Cl—C$_6$H$_4$ | CH$_3$ | H |
| 76.5. | N=CR$_4$ | CH$_3$ | 4-Br—C$_6$H$_4$ | CH$_3$ | H |
| 76.6. | N=CR$_4$ | CH$_3$ | 4-CH$_3$O—C$_6$H$_4$ | CH$_3$ | H |
| 76.7. | N=CR$_4$ | CH$_3$ | 4-CH$_3$CH$_2$O—C$_6$H$_4$ | CH$_3$ | H |
| 76.8. | N=CR$_4$ | CH$_3$ | 3-CF$_3$—C$_6$H$_4$ | CH$_3$ | H |
| 76.9. | N=CR$_4$ | CH$_3$ | CH$_3$ | CH$_3$ | H |
| 76.10. | N=CR$_4$ | CH$_3$ | OCH(CH$_3$)$_2$ | CH$_3$ | H |
| 76.11. | N=CR$_4$ | CH$_3$ | 4-CH$_3$—C$_6$H$_4$ | CH$_3$ | CH$_3$ |
| 76.12. | N=CR$_4$ | CH$_3$ | 4-CH$_3$CH$_2$—C$_6$H$_4$ | CH$_3$ | CH$_3$ |
| 76.13. | N=CR$_4$ | CH$_3$ | 4-F—C$_6$H$_4$ | CH$_3$ | CH$_3$ |
| 76.14. | N=CR$_4$ | CH$_3$ | 4-Cl—C$_6$H$_4$ | CH$_3$ | CH$_3$ |
| 76.15. | N=CR$_4$ | CH$_3$ | 4-Br—C$_6$H$_4$ | CH$_3$ | CH$_3$ |
| 76.16. | N=CR$_4$ | CH$_3$ | 4-CH$_3$O—C$_6$H$_4$ | CH$_3$ | CH$_3$ |
| 76.17. | N=CR$_4$ | CH$_3$ | 4-CH$_3$CH$_2$O—C$_6$H$_4$ | CH$_3$ | CH$_3$ |
| 76.18. | N=CR$_4$ | CH$_3$ | 3-CF$_3$—C$_6$H$_4$ | CH$_3$ | CH$_3$ |
| 76.19. | N=CR$_4$ | CH$_3$ | CH$_3$ | CH$_3$ | CH$_3$ |
| 76.20. | N=CR$_4$ | CH$_3$ | OCH(CH$_3$)$_2$ | CH$_3$ | CH$_3$ |

Formulations may be prepared analogously to those described for example in WO 97/33890.

Biological Examples

Example B-1

Effect against *Puccinia graminis* on Wheat a) Residual Protective Action

Wheat plants are sprayed to drip point, 6 days after sowing, with an aqueous spray liquor prepared from wettable powder of the active ingredient (0.02% active substance), and infected 24 hours later with a uredospore suspension of the fungus. After an incubation period of 48 hours (conditions: 95 to 100% relative atmospheric humidity at 20°), the plants are placed in a greenhouse at 22°. 12 days after infection, the fungal attack is evaluated.

b) Systemic Action

An aqueous spray liquor prepared from wettable powder of the active ingredient (0.006% active substance, based on the volume of soil) is poured onto wheat plants 5 days after sowing. Care is taken that the spray liquor does not come into contact with the parts of the plant that are above ground. 48 hours later, the plants are infected with a uredospore suspension of the fungus. After an incubation period of 48 hours (conditions: 95 to 100% relative atmospheric humidity at 20°), the plants are placed in a greenhouse at 22°. 12 days after infection, the fungal attack is evaluated.

Compounds from the tables show good effect.

Example B-2

Effect against *Phytophthora infestans* on Tomatoes a) Residual Protective Action Tomato plants are sprayed to drip point, after cultivation for 3 weeks, with an aqueous spray liquor prepared from wettable powder of the active ingredient (0.02% active substance), and infected 24 hours later with a sporangia suspension of the fungus. Evaluation of the fungal attack takes place 5 days after infection, during which period conditions of 90 to 100% relative atmospheric humidity and a temperature of 20° are maintained.

b) Systemic Action

An aqueous spray liquor prepared from wettable powder of the active ingredient (0.006% active substance, based on the volume of soil) is poured onto tomato plants which have been cultivated for three weeks. Care is taken that the spray liquor does not come into contact with the parts of the plant that are above ground. 48 hours later, the plants are infected with a sporangia suspension of the fungus. Evaluation of the fungal attack takes place 5 days after infection, during which period conditions of 90 to 100% relative atmospheric humidity and a temperature of 20° are maintained.

Compounds from the tables show good effect.

Example B-3

Residual Protective Action Against *Cercospora arachidicola* on Peanuts

Peanut plants of 10 to 15 cm height are sprayed to drip point with an aqueous spray liquor prepared from wettable powder of the active ingredient (0.02% active substance), and infected 48 hours later with a conidia suspension of the fungus. The plants are incubated for 72 hours at 21° and at high atmospheric humidity and subsequently placed in a greenhouse until the typical leaf spots appear. Evaluation of the efficacy of the active substance takes place 12 days after infection and is based on the number and size of the leaf spots.

Compounds from the tables show good effect.

Example B-4

Effect Against *Plasmopara viticola* on Vines

Vine seedlings at the 4 to 5 leaf stage are sprayed to drip point with an aqueous spray liquor prepared from wettable powder of the active ingredient (0.02% active substance), and infected 24 hours later with a sporangia suspension of the fungus. Evaluation of the fungal attack takes place 6 days after infection, during which period conditions of 95 to 100% relative atmospheric humidity and a temperature of 20° are maintained.

Compounds from the tables show good effect.

Example B-5

Effect Against *Colletotrichum lagenarium* on Cucumbers

Cucumber plants are sprayed after cultivation for 2 weeks with a spray liquor prepared from wettable powder of the active ingredient (concentration 0.002%). After 2 days, the plants are infected with a spore suspension (1.5×10⁵ spores/ml) of the fungus and incubated for 36 hours at 23° C. and at high atmospheric humidity. Incubation is then continued at normal atmospheric humidity and at ca. 22° C. The fungal attack occurring is evaluated 8 days after infection.

Compounds from the tables show good effect.

Example B-6

Residual Protective Action Against *Venturia inaegualis* on Apples

Apple cuttings with fresh shoots of 10 to 20 cm length are sprayed to drip point with an aqueous spray liquor prepared from wettable powder of the active ingredient (0.02% active substance), and infected 24 hours later with a conidia suspension of the fungus. The plants are incubated for 5 days at 90 to 100% relative atmospheric humidity and placed in a greenhouse at 20 to 24° for a further 10 days. 12 days after infection, the fungal attack is evaluated.

Compounds from the tables show good effect.

Example B-7

Effect Against *Erysiphe graminis* on Barley a) Residual Protective Action

Barley plants of approximately 8 cm height are sprayed to drip point with an aqueous spray liquor prepared from wettable powder of the active ingredient (0.02% active substance), and dusted 3 to 4 hours later with conidia of the fungus. The infected plants are placed in a greenhouse at 22°. 12 days after infection, the fungal attack is evaluated.

Compounds from the tables show good effect.

b) Systemic Action

An aqueous spray liquor prepared from wettable powder of the active ingredient (0.002% active substance, based on the volume of soil) is poured onto barley plants of approximately 8 cm height. Care is taken that the spray liquor does not come into contact with the parts of the plant that are above ground. 48 hours later, the plants are dusted with conidia of the fungus. The infected plants are placed in a greenhouse at 22°. 12 days after infection, the fungal attack is evaluated.

Compounds from the tables show good effect.

Example B-8

Effect Against *Podosphaera leucotricha* on Apple Shoots

Apple cuttings with fresh shoots of ca. 15 cm length are sprayed with a spray liquor (0.06% active substance). After 24 hours, the treated plants are infected with a conidia suspension of the fungus and placed in climate-controlled chamber at 70% relative atmospheric humidity and 20° C. 12 days after infection, the fungal attack is evaluated.

Compounds from the tables show good effect.

Biological Examples

B. Insecticidal Action

Example B-9

Effect Against *Aphis craccivora*

Pea seedlings are infected with *Aphis craccivora*, subsequently sprayed with a spray liquor containing 100 ppm active ingredient, and then incubated at 20°. Using a comparison between the number of dead leaf aphids on the treated and the untreated plants 3 and 6 days later, the percentage reduction in population (% action) is determined.

Compounds from the tables show good effect in this test, i.e. a death rate of more than 80%.

Example B-10

Effect Against *Diabrotica balteata*

Maize seedlings are sprayed with an aqueous emulsion spray liquor containing 400 ppm active ingredient. After the spray coating has begun to dry, the seedlings are colonized with 10 larvae of the second stage of *Diabrotica balteata* and then placed in a plastic container. Using a comparison between the number of dead larvae on the treated and the untreated plants 6 days later, the percentage reduction in population (% action) is determined.

Compounds from the tables show good effect in this test.

Example B-11
Effect Against *Heliothis virescens*

Young soya plants are sprayed with an aqueous emulsion spray liquor containing 100 ppm active ingredient. After the spray coating has begun to dry, the plants are colonized with 10 grubs of the first stage of *Heliothis virescens* and then placed in a plastic container. Using a comparison between the number of dead grubs and the feeding damage on the treated and the untreated plants 6 days later, the percentage reduction in population and in feeding damage (% action) is determined.

Compounds from the tables show good effect in this test.

Example B-12
Effect Against *Spodoptera littoralis*

Young soya plants are sprayed with an aqueous emulsion spray liquor containing 100 ppm active ingredient. After the spray coating has begun to dry, the plants are colonized with 10 grubs of the third stage of *Spodoptera littoralis* and then placed in a plastic container. Using a comparison between the number of dead grubs and the feeding damage on the treated and the untreated plants 3 days later, the percentage reduction in population and in feeding damage (% action) is determined.

Compounds from the tables show good effect in this test.

Example B-13
Effect Against *Nilaparvata lugens*

Rice plants are sprayed with an aqueous emulsion spray liquor containing 100 ppm active ingredient. After the spray coating has begun to dry, the rice plants are colonized with plant- and leaf-hopper larvae of the second and third stage. Evaluation takes place 21 days later. Using a comparison between the number of surviving plant- and leaf-hoppers on the treated and the untreated plants, the percentage reduction in population (% action) is determined.

Compounds from the tables show over 90% effect.

Example B-14
Effect Against *Plutella xylostella* Grubs

Young cabbage plants are sprayed with an aqueous emulsion spray liquor containing 100 ppm active ingredient. After the spray coating has begun to dry, the cabbage plants are colonized with 10 grubs of the third stage of *Plutella xylostella* and placed in a plastic container. Evaluation takes place 3 days later. Using a comparison between the number of dead grubs and the feeding damage on the treated and the untreated plants, the percentage reduction in population and in feeding damage (% action) is determined.

Compounds from the tables show good effect.

Example B-15
Effect Against *Musca domestica*

A sugar cube is treated with a solution of the test substance so that, after drying over night, the concentration of test substance in the sugar is 250 ppm. This treated cube is placed on an aluminium dish with a wet cotton-wool pad and 10 *Musca domestica* adults of an OP-resistant strain, covered with a beaker and incubated at 25° C. After 24 hours, the mortality rate is determined.

Compounds from the tables show good effect.

Biological Examples
C. Acaricidal Action

B-16
Effect Against *Tetranychus urticae*

Young bean plants are colonized with a mixed population of *Tetranychus urticae* and sprayed one day later with an aqueous emulsion spray liquor containing 400 ppm active ingredient. The plants are subsequently incubated for 6 days at 25° C. and then evaluated. Using a comparison between the number of dead eggs, larvae and adults on the treated and the untreated plants, the percentage reduction in population (% action) is determined.

Compounds from the tables show good effect.

Example B-17
Effect on Mixed Populations of *Tetranychus cinnabarinus* Dilution Series Bush beans at the second leaf stage are colonized with a mixed population (eggs, larvae/nymphs, adults) of an OP-tolerant strain of *Tetranychus cinnabarinus*. 24 hours after infection, the products are applied to the plants at dosages of 200, 100, 50 mg AS/l in an automatic spray cabin. The substances are formulated and diluted with water to the corresponding dosages. The test is evaluated 2 and 7 days after application for the percentage mortality of eggs, larvae/nymphs and adults. Compounds from the tables exhibit over 70% mortality in dilutions up to 50 mg AS/liter.

Example B-18
Effect Against *Boophilus microplus*

Adult female ticks which have sucked themselves full are adhered to a PVC plate, covered with a cotton-wool pad, and then 10 ml of test solution containing 125 ppm active ingredient is poured on. The cotton-wool pad is removed and the ticks are incubated for 4 weeks to lay eggs. The effect is shown either as mortality or sterility of females or as ovicidal action of eggs.

What is claimed is:
1. A compound of formula I, wherein
A is a group $OCHR_4$ or $N=CR_4$;
Y is O,
$R_1$ is $C_1$–$C_6$-alkyl;
$R_2$ is $C_1$–$C_6$-alkyl or $C_1$–$C_6$-alkyl substituted by 1 to 5 fluorine atoms;
$R_3$ is $C_1$–$C_6$-alkyl, $C_1$–$C_6$-alkoxy, $C_3$–$C_6$-cycloalkyl, $C_3$–$C_6$-cycloalkoxy, $C_2$–$C_6$-alkenyl, $C_2$–$C_6$-alkenyloxy, $C_2$–$C_6$-alkynyl, $C_2$–$C_6$-alkynyloxy, $C_1$–$C_6$-alkoxycarbonyl, CN or halogen, whereby the above-mentioned groups, with the exception of CN and halogen, may be substituted by one or more identical or different substitutents selected from the group comprising halogen, cyano, nitro, $C_1$–$C_6$-alkoxycarbonyl, $C_1$–$C_6$-alkoxy, $C_1$–$C_6$-alkylthio, aminocarbonyl, $C_1$–$C_6$-alkylaminocarbonyl, di-$C_1$–$C_6$-alkylaminocarbonyl, $C_2$–$C_6$-alkenyloxy, $C_3$–$C_6$- cycloalkyl, $C_3$–$C_6$-cycloalkyloxy, heterocyclyl, heterocyclyloxy, aryl, aryloxy, heteroaryl, heteroaryloxy, whereby the cyclic radicals in turn may be substituted by one or more identical or different substitutents selected from the group comprising halogen, cyano, nitro, $C_1$–$C_6$-alkyl, $C_1$–$C_6$halogenoalkyl, $C_1$–$C_6$-alkoxy, $C_1$–$C_6$-halogenoalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, optionally substituted benzyl, optionally substituted benzyloxy, optionally substituted aryl, optionally substituted aryloxy, optionally substituted heteroaryl and optionally substituted heteroaryloxy, whereby the optionally substituted aromatic groups are unsubstituted or mono- to tri-substituted by the same or different substituents selected from halogen, $C_1$–$C_6$-alkyl, $C_1$–$C_6$-halogenoalkyl, $C_1$–$C_6$-alkoxy, $C_1$–$C_6$-halogenoalkoxy, $C_2$–$C_6$-alkenyl, $C_2$–$C_6$-alkenyloxy, $C_2$–$C_6$-alkynyl, $C_3$–$C_6$-alkynyloxy, $C_1$–$C_6$-alkoxycarbonyl, CN or OCN; or $R_3$ is aryl, heteroaryl, heterocyclyl, aryloxy, heteroaryloxy or heterocyclyloxy, whereby the above-mentioned groups may be substituted by one or more identical or different substitutents selected from the group comprising halogen, $C_1$–$C_6$-alkoxy, halogeno-$C_1$–$C_6$-alkoxy, $C_1$–$C_6$-alkylthio, halogeno-$C_1$–$C_6$-alkylthio, $C_1$–$C_6$-alkylsulfinyl, halogeno-$C_1$–$C_6$-alkylsulfinyl, $C_1$–$C_6$-alkylsulfonyl, halogeno-$C_1$–$C_6$-alkylsulfonyl, $C_1$–$C_6$-alkylcarbonyl, halogeno-$C_1$–$C_6$-alkylcarbonyl, $C_1$–$C_6$-alkoxycarbonyl, halogeno-$C_1$–$C_6$-alkoxycarbonyl, $C_1$–$C_6$-alkylamino-carbonyl, di-($C_1$–$C_6$-alkyl)-aminocarbonyl, whereby the alkyl groups may be identical or different, $C_1$–$C_6$-alkylaminothiocarbonyl, di-($C_1$–$C_6$-alkyl)-aminothiocarbonyl, whereby the alkyl groups may be identical or different, $C_1$–$C_6$-alkylamino, di-($C_1$–$C_6$-alkyl)-amino, $NO_2$, an unsubstituted $C_1$–$C_4$-alkylenedioxy group or one which is substituted once to four times by $C_1$–$C_4$-alkyl and/or by halogen, or CN, $SF_3$ and $QR_5$;

Q is a direct bond, O, O($C_1$–$C_6$-alkylene), ($C_1$–$C_6$-alkylene)O, S(=O)p, S(=O)p($C_1$–$C_6$-alkylene), ($C_1$–$C_6$-alkylene)S(=O)p, $C_1$–$C_8$-alkylene, $C_2$–$C_6$-alkenylene or $C_2$–$C_6$-alkynylene;

$R_5$ is a $C_2$–$C_6$-alkenyl or $C_2$–$C_6$-alkynyl group either unsubstituted or substituted by 1 to 3 halogen atoms, a ($C_1$–$C_4$-alkyl)$_3$Si group, whereby the alkyl groups may be identical or different, CN, an unsubstituted or mono- to penta-substituted $C_3$–$C_6$-cycloalkyl, aryl, hetaryl or heterocyclyl group, whereby the substituents are selected from the group comprising halogen, $C_1$–$C_6$-alkyl, halogeno-$C_1$–$C_6$-alkyl, $C_1$–$C_6$-alkoxy, halogeno-$C_1$–$C_6$-alkoxy, phenoxy and CN;

p is 0, 1 or 2;

$R_4$ is methyl, ethyl or cyclopropyl; and $R_6$ is hydrogen or methyl;

with the proviso that when $R_1$ is $C_1$–$C_6$-alkyl, $R_6$ is hydrogen, $R_4$ is methyl or ethyl and $R_2$ is $C_1$–$C_6$-alkyl or $C_1$–$C_6$-alkyl substituted by 1 to 5 fluorine atoms, then $R_3$ is other than $C_1$–$C_6$-alkoxycarbonyl.

2. A compound of formula I according to claim 1, wherein A is the group $OCHR_4$.

3. A compound of formula I according to claim 1, wherein A is the group $N=CR_4$.

4. A compound of formula I according to claim 1, wherein $R_1$ is methyl or ethyl, and $R_2$ is methyl, ethyl, fluoromethyl or trifluoroethyl.

5. A compound of formula I according to claim 1, wherein $R_3$ is $C_{1-6}$-alkyl, $C_1$–$C_6$-alkoxy, $C_2$–$C_6$-alkenyl, $C_{2-6}$-alkenyloxy, $C_2$–$C_6$-alkynyl, $C_3$–$C_6$-alkynyloxy, $C_3$–$C_6$-cycloalkyl, $C_3$–$C_6$-cycloalkyloxy or $C_1$–$C_6$-alkoxycarbonyl, whereby the above-mentioned groups may be partly or fully halogenated; in addition, CN, OCN or halogen.

6. A compound of formula I according to claim 1, wherein $R_3$ is phenyl which is unsubstituted or mono- to tri-substituted by identical or different subsituents from halogen, $C_1$–$C_6$-alkyl, $C_1$–$C_6$-halogenoalkyl, $C_1$–$C_6$-alkoxy, $C_1$–$C_6$-halogenoalkoxy, $C_2$–$C_6$-alkenyl, $C_2$–$C_6$-alkenyloxy, $C_2$–$C_6$-alkynyl, $C_3$–$C_6$-alkynyloxy, $C_1$–$C_6$-alkoxycarbonyl, CN, OCN, optionally substituted benzyl, optionally substituted phenyl or optionally substituted phenoxy, whereby the optionally substituted aromatic groups are unsubstituted or mono- to tri-substituted by identical or different substituents from halogen, $C_1$–$C_6$-alkyl, $C_1$–$C_6$-halogenoalkyl, $C_1$–$C_6$-alkoxy, $C_1$–$C_6$-halogenoalkoxy, $C_2$–$C_6$-alkenyl, $C_2$–$C_6$-alkenyloxy, $C_2$–$C_6$-alkynyl, $C_3$–$C_6$-alkynyloxy, $C_1$–$C_6$-alkoxycarbonyl, CN or OCN.

7. A compound of formula I according to claim 1, wherein $R_3$ is pyridyl, pyrimidinyl, furyl, thienyl, oxazolyl, isoxazolyl, thiazolyl, isothiazolyl, imidazolyl, pyrazolyl, which are unsubstituted or mono- to tri-substituted by identical or different subsituents from halogen, cyano, nitro, aminocarbonyl, $C_1$–$C_4$-alkyl, $C_1$–$C_4$-halogenalkyl, $C_1$–$C_4$-alkylcarbonyl, $C_1$–$C_4$-alkylsulfonyl, $C_{1-C6}$-alkylsulfoxyl, $C_3$–$C_6$-cycloalkyl, optionally substituted arylcarbonyl, $C_1$–$C_4$-alkoxy, $C_1$–$C_4$-halogenalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl or $C_2$–$C_6$-alkenyl.

8. A compound according to claim 1, wherein $R_4$ is cyclopropyl.

9. A compound according to claim 1, wherein $R_3$ is CN or halogen, or $R_3$ is $C_1$–$C_6$-alkyl, $C_1$–$C_6$-alkoxy, $C_3$–$C_6$-cycloalkyl, $C_3$–$C_6$-cycloalkoxy, $C_2$–$C_6$-alkenyl, $C_2$–$C_6$-alkenyloxy, $C_2$–$C_6$-alkynyl, or $C_2$–$C_6$-alkynyloxy wherein the above-mentioned groups may be substituted by one or more identical or different substitutents selected from the group comprising halogen, cyano, nitro, $C_1$–$C_6$-alkoxycarbonyl, $C_1$–$C_6$-alkoxy, $C_1$–$C_6$-alkylthio, aminocarbonyl, $C_1$–$C_6$-alkylaminocarbonyl, di-$C_1$–$C_6$-alkylaminocarbonyl, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, heteroaryl, heteroaryloxy, wherein the cyclic radicals in turn may be substituted by one or more identical or different substitutents selected from the group comprising halogen, cyano, nitro, $C_1$–$C_6$-alkyl, $C_1$–$C_6$halogenoalkyl, $C_1$–$C_6$-alkoxy, $C_1$–$C_6$-halogenoalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, optionally substituted benzyl, optionally substituted benzyloxy, optionally substituted aryl, optionally substituted aryloxy, optionally substituted heteroaryl and optionally substituted heteroaryloxy, whereby the optionally substituted aromatic groups are unsubstituted or mono- to tri-substituted by the same or different substituents selected from halogen, $C_1$–$C_6$-alkyl, $C_1$–$C_6$-halogenoalkyl, $C_1$–$C_6$-alkoxy, $C_1$–$C_6$-halogenoalkoxy, $C_2$–$C_6$-alkenyl, $C_2$–$C_6$-alkenyloxy, $C_2$–$C_6$-alkynyl, $C_3$–$C_6$-alkynyloxy, $C_1$–$C_6$-alkoxycarbonyl, CN or OCN.

10. A compound according to claim 1, wherein $R_3$ is aryl, heteroaryl, heterocyclyl, aryloxy, heteroaryloxy or heterocyclyloxy, whereby the above-mentioned groups may be substituted by one or more identical or different substitutents selected from the group comprising halogen, $C_1$–$C_6$-alkoxy, halogeno-$C_1$–$C_6$-alkoxy, $C_1$–$C_6$-alkylthio, halogeno-$C_1$–$C_6$-alkylthio, $C_1$–$C_6$-alkylsulfinyl, halogeno-$C_1$–$C_6$-alkylsulfinyl, $C_1$–$C_6$-alkylsulfonyl, halogeno-$C_1$–$C_6$-alkylsulfonyl, $C_1$–$C_6$-alkylcarbonyl, halogeno-$C_1$–$C_6$-alkylcarbonyl, $C_1$–$C_6$-alkoxycarbonyl, halogeno-$C_1$–$C_6$-alkoxycarbonyl, $C_1$–$C_6$-alkylamino-carbonyl, di-($C_1$–$C_6$-alkyl)-aminocarbonyl, whereby the alkyl groups may be identical or different, $C_1$–$C_6$-alkylaminothiocarbonyl, di-($C_1$–$C_6$-alkyl)-aminothiocarbonyl, whereby the alkyl groups may be identical or different, $C_1$–$C_6$-alkylamino, di-($C_1$–$C_6$-alkyl)-amino, $NO_2$, an unsubstituted $C_1$–$C_4$-alkylenedioxy group or one which is substituted once to four times by $C_1$–$C_4$-alkyl and/or by halogen, or CN, $SF_3$ and $QR_5$.

11. A compound of formula I

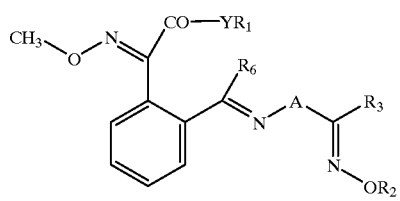

(I)

wherein

A is a group $OCHR_4$ or $N=CR_4$;

Y is O;

$R_1$ is $C_1$–$C_6$-alkyl;

$R_2$ is $C_1$–$C_6$-alkyl or $C_1$–$C_6$-alkyl substituted by 1 to 5 fluorine atoms;

$R_3$ is CN or halogen, or $R_3$ is $C_1$–$C_6$-alkyl, $C_1$–$C_6$-alkoxy, $C_3$–$C_6$-cycloalkyl, $C_3$–$C_6$-cycloalkoxy, $C_2$–$C_6$-alkenyl, $C_2$–$C_6$-alkenyloxy, $C_2$–$C_6$-alkynyl or $C_2$–$C_6$-alkynyloxy, whereby the above-mentioned groups may be substituted by one or more identical or different substitutents selected from the group comprising halogen, cyano, nitro, $C_1$–$C_6$-alkoxycarbonyl, $C_1$–$C_6$-alkoxy, $C_1$–$C_6$-alkylthio, aminocarbonyl, $C_1$–$C_6$-alkylaminocarbonyl, di-$C_1$–$C_6$-alkylaminocarbonyl, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, heteroaryl, heteroaryloxy, whereby the cyclic radicals in turn may be substituted by one or more identical or different substitutents selected from the group comprising halogen, cyano, nitro, $C_1$–$C_6$-alkyl, $C_1$–$C_6$halogenoalkyl, $C_1$–$C_6$-alkoxy, $C_1$–$C_6$-halogenoalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, optionally substituted benzyl, optionally substituted benzyloxy, optionally substituted aryl, optionally substituted aryloxy, optionally substituted heteroaryl and optionally substituted heteroaryloxy, whereby the optionally substituted aromatic groups are unsubstituted or mono- to tri-substituted by the same or different substituents selected from halogen, $C_1$–$C_6$-alkyl, $C_1$–$C_6$-halogenoalkyl, $C_1$–$C_6$-alkoxy, $C_1$–$C_6$-halogenoalkoxy, $C_2$–$C_6$-alkenyl, $C_2$–$C_6$-alkenyloxy, $C_2$–$C_6$-alkynyl, $C_3$–$C_6$-alkynyloxy, $C_1$–$C_6$-alkoxycarbonyl, CN or OCN; or $R_3$ is aryl, heteroaryl, heterocyclyl, aryloxy, heteroaryloxy or heterocyclyloxy, whereby the above-mentioned groups may be substituted by one or more identical or different substitutents selected from the group comprising halogen, $C_1$–$C_6$-alkoxy, halogeno-$C_1$–$C_6$-alkoxy, $C_1$–$C_6$-alkylthio, halogeno-$C_1$–$C_6$-alkylthio, $C_1$–$C_6$-alkylsulfinyl, halogeno-$C_1$–$C_6$-alkylsulfinyl, $C_1$–$C_6$-alkylsulfonyl, halogeno-$C_1$–$C_6$-alkylsulfonyl, $C_1$–$C_6$-alkylcarbonyl, halogeno-$C_1$–$C_6$-alkylcarbonyl, $C_1$–$C_6$-alkoxycarbonyl, halogeno-$C_1$–$C_6$-alkoxycarbonyl, $C_1$–$C_6$-alkylamino-carbonyl, di-($C_1$–$C_6$-alkyl)-aminocarbonyl, whereby the alkyl groups may be identical or different, $C_1$–$C_6$-alkylaminothiocarbonyl, di-($C_1$–$C_6$-alkyl)-aminothiocarbonyl, whereby the alkyl groups may be identical or different, $C_1$–$C_6$-alkylamino, di-($C_1$–$C_6$-alkyl)-amino, $NO_2$, an unsubstituted $C_1$–$C_4$-alkylenedioxy group or one which is substituted once to four times by $C_1$–$C_4$-alkyl and/or by halogen, or CN, $SF_3$ and $QR_5$;

Q is a direct bond, O, O($C_1$–$C_6$-alkylene), ($C_1$–$C_6$-alkylene)O, S(=O)p, S(=O)p($C_1$–$C_6$-alkylene), ($C_1$–$C_6$-alkylene)S(=O)p, $C_1$–$C_8$-alkylene, $C_2$–$C_6$-alkenylene or $C_2$–$C_6$-alkynylene;

$R_5$ is a $C_2$–$C_6$-alkenyl or $C_2$–$C_6$-alkynyl group either unsubstituted or substituted by 1 to 3 halogen atoms, a ($C_1$–$C_4$-alkyl)$_3$Si group, whereby the alkyl groups may be identical or different, CN, an unsubstituted or mono- to penta-substituted $C_3$–$C_6$-cycloalkyl, aryl, hetaryl or heterocyclyl group, whereby the substituents are selected from the group comprising halogen, $C_1$–$C_6$-alkyl, halogeno-$C_1$–$C_6$-alkyl, $C_1$–$C_6$-alkoxy, halogeno-$C_1$–$C_6$-alkoxy, phenoxy and CN;

p is 0, 1 or 2;

$R_4$ is methyl, ethyl or cyclopropyl; and $R_6$ is hydrogen or methyl.

12. A compound according to claim 11, wherein $R_3$ is $C_1$–$C_6$-alkyl, $C_1$–$C_6$-alkoxy, $C_2$–$C_6$-alkenyl, $C_2$–$C_6$-alkenyloxy, $C_2$–$C_6$-alkynyl, $C_3$–$C_6$-alkynyloxy, $C_3$–$C_6$-cycloalkyl or $C_3$–$C_6$-cycloalkyloxy, whereby the above-mentioned groups may be partly or fully halogenated.

13. A compound according to claim 11, wherein $R_3$ is aryl, heteroaryl, heterocyclyl, aryloxy, heteroaryloxy or heterocyclyloxy, whereby the above-mentioned groups may be substituted by one or more identical or different substitutents selected from the group comprising halogen, $C_1$–$C_6$-alkoxy, halogeno-$C_1$–$C_6$-alkoxy, $C_1$–$C_6$-alkylthio, halogeno-$C_1$–$C_6$-alkylthio, $C_1$–$C_6$-alkylsulfinyl, halogeno-$C_1$–$C_6$-alkylsulfinyl, $C_1$–$C_6$-alkylsulfonyl, halogeno-$C_1$–$C_6$-alkylsulfonyl, $C_1$–$C_6$-alkylcarbonyl, halogeno-$C_1$–$C_6$-alkylcarbonyl, $C_1$–$C_6$-alkoxycarbonyl, halogeno-$C_1$–$C_6$-alkoxycarbonyl, $C_1$–$C_6$-alkylamino-carbonyl, di-($C_1$–$C_6$-alkyl)-aminocarbonyl, whereby the alkyl groups may be identical or different, $C_1$–$C_6$-alkylaminothiocarbonyl, di-($C_1$–$C_6$-alkyl)-aminothiocarbonyl, whereby the alkyl groups may be identical or different, $C_1$–$C_6$-alkylamino, di-($C_1$–$C_6$-alkyl)-amino, $NO_2$, an unsubstituted $C_1$–$C_4$-alkylenedioxy group or one which is substituted once to four times by $C_1$–$C_4$-alkyl and/or by halogen, or CN, $SF_3$ and $QR_5$.

14. A compound according to claim 11, wherein $R_3$ is CN or halogen.

15. A compound according to claim 11, wherein $R_4$ is cyclopropyl.

16. A composition for the control of pests, containing as the active ingredient an effective quantity of a compound according to claim 1, together with an appropriate carrier material; wherein the pests are selected from the group consisting of phytopathogenic fungi, insects, acarids and combinations thereof.

17. A process for the control and prevention of plant pests, comprising the step of applying a compound according to claim 1 to the pests or to their locus; wherein the pests are selected from the group consisting of phytopathogenic fungi, insects, acarids and combinations thereof.

* * * * *